US007087200B2

(12) United States Patent
Taboas et al.

(10) Patent No.: US 7,087,200 B2
(45) Date of Patent: Aug. 8, 2006

(54) CONTROLLED LOCAL/GLOBAL AND MICRO/MACRO-POROUS 3D PLASTIC, POLYMER AND CERAMIC/CEMENT COMPOSITE SCAFFOLD FABRICATION AND APPLICATIONS THEREOF

(75) Inventors: Juan Taboas, Ann Arbor, MI (US); Rachel D Maddox, Ann Arbor, MI (US); Paul H Krebsbach, Ann Arbor, MI (US); Scott J Hollister, Ann Arbor, MI (US); Tien-Min Gabriel Chu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 240 days.

(21) Appl. No.: 10/178,292

(22) Filed: Jun. 24, 2002

(65) Prior Publication Data

US 2003/0006534 A1   Jan. 9, 2003

Related U.S. Application Data

(60) Provisional application No. 60/300,353, filed on Jun. 22, 2001, now abandoned.

(51) Int. Cl.
  *B29C 33/38* (2006.01)
  *B29C 39/02* (2006.01)
  *B29C 44/02* (2006.01)

(52) U.S. Cl. .................. 264/49; 164/47; 264/50; 264/51; 264/53; 264/212; 264/219; 264/232; 264/255; 264/299; 264/317; 264/328.1; 623/11.11

(58) Field of Classification Search .............. 164/47; 264/49, 51, 219, 220, 222, 255, 317, 212, 264/232, 299, 328.1
See application file for complete search history.

(56) References Cited

U.S. PATENT DOCUMENTS

| 5,227,979 A | 7/1993 | Fukuhira et al. |
| 5,680,317 A | 10/1997 | Watanabe |
| 5,713,410 A * | 2/1998 | LaSalle et al. ............... 164/516 |
| 5,741,215 A * | 4/1998 | D'Urso ....................... 600/407 |
| 5,762,125 A | 6/1998 | Mastrotio |
| 5,980,812 A * | 11/1999 | Lawton ....................... 264/401 |
| 6,013,853 A | 1/2000 | Athanasiou et al. |
| 6,143,293 A | 11/2000 | Weiss et al. |
| 6,165,193 A * | 12/2000 | Greene et al. .............. 606/191 |
| 6,192,327 B1 | 2/2001 | Nishiyama et al. |
| 6,210,162 B1 * | 4/2001 | Chishti et al. .............. 433/213 |
| 6,233,499 B1 | 5/2001 | Matsumoto |
| 6,309,215 B1 * | 10/2001 | Phan et al. ................... 433/24 |

OTHER PUBLICATIONS

International Search Report mailed Oct. 2, 2002.
International Search Report mailed Feb. 26, 2003.

* cited by examiner

*Primary Examiner*—Allan R. Kuhns

(57) ABSTRACT

An indirect solid free form scaffold manufacturing technique is provided. More particularly, the present invention provides a set of molds, casting methods, mold removals, and surface modification techniques that are compatible with image-based design methods and with solvent, melt, and slurry casting of polymers and ceramics.

44 Claims, 23 Drawing Sheets

CONTROLLED LOCAL/GLOBAL AND MICRO/MACRO-POROUS 3D PLASTIC, POLYMER AND CERAMIC/CEMENT COMPOSITE SCAFFOLD FABRICATION AND APPLICATIONS THEREOF

CROSS-REFERENCE TO RELATED APPLICATIONS

This application claims the benefit of U.S. Provisional Application No. 60/300,353, filed Jun. 22, 2001 now abandoned.

FIELD OF THE INVENTION

The present invention relates to methods for producing three dimensional structures with designed and controlled micro-porous and macro-porous locally and globally pored internal architectures using solid free form fabrication techniques.

BACKGROUND OF THE INVENTION

Tissue reconstruction, regeneration of damaged tissues and organs, artificial organ production, and fabrication of living tissue constructs for proteomic, drug interaction, drug delivery, and pathogen analyses often requires the fabrication of tissue templates (scaffolds). Control over structure porosity in such scaffolds is critical. Precise control of scaffold porosity and internal pore architecture parameters (e.g. pore geometry, size, interconnectivity, orientation, and branching) is necessary to maximize nutrient diffusion, interstitial fluid and blood flow, to control cell growth and function, to manipulate tissue differentiation, and to optimize scaffold physical function and regenerated tissue physical properties.

The ability to manufacture with a range of materials and the ability to control the surface properties of the materials is also critical. The material employed allows control of scaffold degradation and mechanical integrity, cell interaction with the scaffold, and cell function. Material surface roughness, charge, hydrophobicity, and stability/dissolution have also been shown to regulate cell function.

Composites of polymer and ceramic are noteworthy because the mixed material composition can confer favorable mechanical properties, including strength via the ceramic phase, toughness and plasticity via the polymer phase, and graded mechanical stiffness. Biologic advantages include enhanced control over cell differentiation and the potential to deliver multiple biofactors, including growth factors, gene therapy vectors, and cells. Composite scaffolds may prove necessary for reconstruction of multi-tissue organs, tissue interfaces, and structural tissues including bone, cartilage, tendon, ligament and muscle.

However, the mechanical property requirements for hard tissue repair are difficult to satisfy using polymer/ceramic blend composites in which the ceramic and polymer components are mixed and occupy the same space. This is because large amounts of ceramic must be incorporated, making fabrication difficult. Therefore, composites with discrete regions of fully sintered HA are desirable for bone/soft tissue interfaces.

Composites scaffolds with discrete regions of materials are desirable for controlling structure mechanical properties, degradation kinetics, and biological interaction, as well as for producing structures that mimic natural tissue properties, structures that deliver several biofactors (drug/gene) vehicles, and living structures that contain multiple tissue components.

Although several manufacturing techniques exist to create scaffolds, precise control of pore geometry and interconnectivity is difficult. Conventional sponge scaffold manufacturing methods are capable of producing structures with locally-porous internal architectures from a diverse array of materials. The local pores in such scaffolds are voids characteristically defined by small struts and plates or spherical and tubular cavities generally less than 300 μm in diameter. These local pores are interconnected within local regions of the scaffold microstructure.

While these local pored scaffolds may include interconnected micro (less than 100 μm wide) pores that may comprise a continuous conduit throughout a scaffold, the pore connectivity is not an intentional result of an a priori global design. Rather, the connectivity is a random product of variable, local void interconnections that are affected by polymer processing parameters. Such random connections may not provide optimal scaffold permeability for tissue ingrowth nor optimal connectivity to maximize regenerated tissue mechanical properties.

Unlike sponge methods, micro-milling, textile, and direct solid free form (SFF) fabrication can be used to create scaffolds with good global pore control. The global pores take the shape of channels with non-random interconnectivity that are designed a priori to interconnect on a global scale across the scaffold. Unlike micro-milling and textile fabrication, full control over global pore architecture in 3D space is available with SFF. Unfortunately, the number of materials that can be used for each direct SFF manufacturing method is limited by the manufacturing process. Additionally, the incorporation of local pores in a direct SFF fabricated global pored scaffold is difficult.

Global and local pores are differentiated based on the extent of non-random designed interconnectivity. These pores may be sub-classified by size as either microporous (width less than 100 μm) or macroporous (width greater than 100 μm). Current direct SFF manufacturing is limited to manufacturing global pores with widths greater than 100 μm because of inherent limitations on the minimum size feature.

Direct SFF fabrication, also known as rapid prototyping, refers to a set of manufacturing processes that consists of building a 3D part in a layered fashion based on a computer representation. The part is often post processed (e.g. cleaning, curing, finishing) to yield the final product.

SFF has been used to mimic the 3D shape of macroscopic structures. However, a versatile method to manufacture biomimetic structures in the microscopic range, for example structures that mimic human trabecular bone or 3D vascular branching, has not been available. Such biomimetic strategies are desirable to replicate native tissue structure and function.

The need for 3D scaffolds with controlled local/global and micro/macro pores is great. However, current 3D local-pore scaffold fabrication methods do not allow fabrication of pores with designed geometry, orientation, branching, interconnectivity, and size. Global-pore manufacturing methods, including current SFF fabrication techniques, are not suitable for varied micro-pore structure fabrication and provide limited incorporation of local-pores within a global-porous structure. Additionally, the need for 3D scaffolds made from a variety of materials is great. Further, control over the discrete spatial location and surface properties of varied materials within the same scaffold is desired.

SUMMARY OF THE INVENTION

A method of fabricating tissue scaffolds and other similar structures is provided. The method includes computationally designing the desired structure, fabricating a mold for the desired structure, casting the desired structure in the mold, and removing the mold from the desired structure. Methods for post modification of the desired structure are presented. The step of computationally designing the desired structure preferably includes at least one computer aided design technique and/or an image based design technique. The step of fabricating the mold for the desired structure preferably includes solid free form techniques such as 3D printing, fused deposition, stereolithography, selective laser sintering, direct material deposition, or layered object manufacturing. The step of post modification of the structure preferably includes stabilized plasma functionalization.

In accordance with the foregoing, the present invention provides three dimensional structures with designed and controlled local-porous and global-porous internal architectures. Enhanced control of global-pore orientation, branching, interconnectivity, size, and geometry is provided compared to current SFF techniques. Additionally, a larger variety of local-pore architectures are possible. The disclosed methods allow for fabrication of structures from more materials than currently possible with existing SFF fabrication and for post fabrication surface modification of these materials. Moreover, methods to fabricate mechanically robust porous composite structures containing a number of plastics or combinations of plastics and ceramic (and/or cements) are provided. These methods provide for 3D structure fabrication from more material blends and combinations of discrete material regions than currently available. Additionally, the mechanical strength of structures fabricated using these methods both in the build direction and at the composite material interface regions is improved. Novel designs and constructs created from these structures are presented for use as tissue regeneration scaffolds, bioreactor culture substrates, perfusion (advection) assisted diffusion exchangers, 3D templates for screening material/cell interaction with identical architectures, and living tissue constructs for screening the effects of pathogens and drugs derived from proteomic data and pharmacology science on human tissues in vitro. The disclosed methods enable the fabrication of engineered tissues that are mechanically and biologically functional. Constructs fabricated with this technology constitute a large reduction in drug screening costs and an advancement in "lab on chip", biosensor, and cell manufactured drug technologies.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiments is merely exemplary in nature and is in no way intended to limit the invention, its application, or uses.

To circumvent the limitations of the prior art and combine the benefits of local pore manufacturing and direct SFF fabrication, an indirect SFF scaffold manufacturing technique is provided. More particularly, the present invention provides a set of molds, casting methods, mold removal, and structure post fabrication modification techniques that are compatible with image-based design (IBD) methods and with solvent, melt, and slurry casting of polymers and ceramics.

The indirect SFF fabrication method of the present invention combines image based design with SFF fabrication to precisely control scaffold architecture and material composition. This method provides simultaneous control of scaffold external shape to match implant site geometry, internal architecture to yield biomimetic structures, and global pore structure in 3D space (interconnectivity, branching, geometry, diameter, and orientation). Additionally, the indirect SFF method is compatible with most local pore polymer scaffold processing techniques, thereby providing inclusion of local pores within a scaffold global pore framework.

The molds and methods of the present invention allow 1) fabrication of discrete composite scaffolds made from materials that have incompatible processing parameters such as sintered ceramics and polymers, 2) fabrication of scaffolds from the largest pool of materials possible, 3) production of local and global pores within one scaffold, and 4) fabrication of structurally biomimetic scaffolds. These multi-pore-architecture scaffolds are ideal for several tissue engineering applications. For example, the global pores may serve as channels to perfuse culture media or augment diffusion of nutrients to cells seeded within local pores. In turn, the local pores provide a potential space for tissue growth. Global pores may also serve as conduits for blood vessel ingrowth or to anchor the scaffold once implanted in a host.

Figure 1:
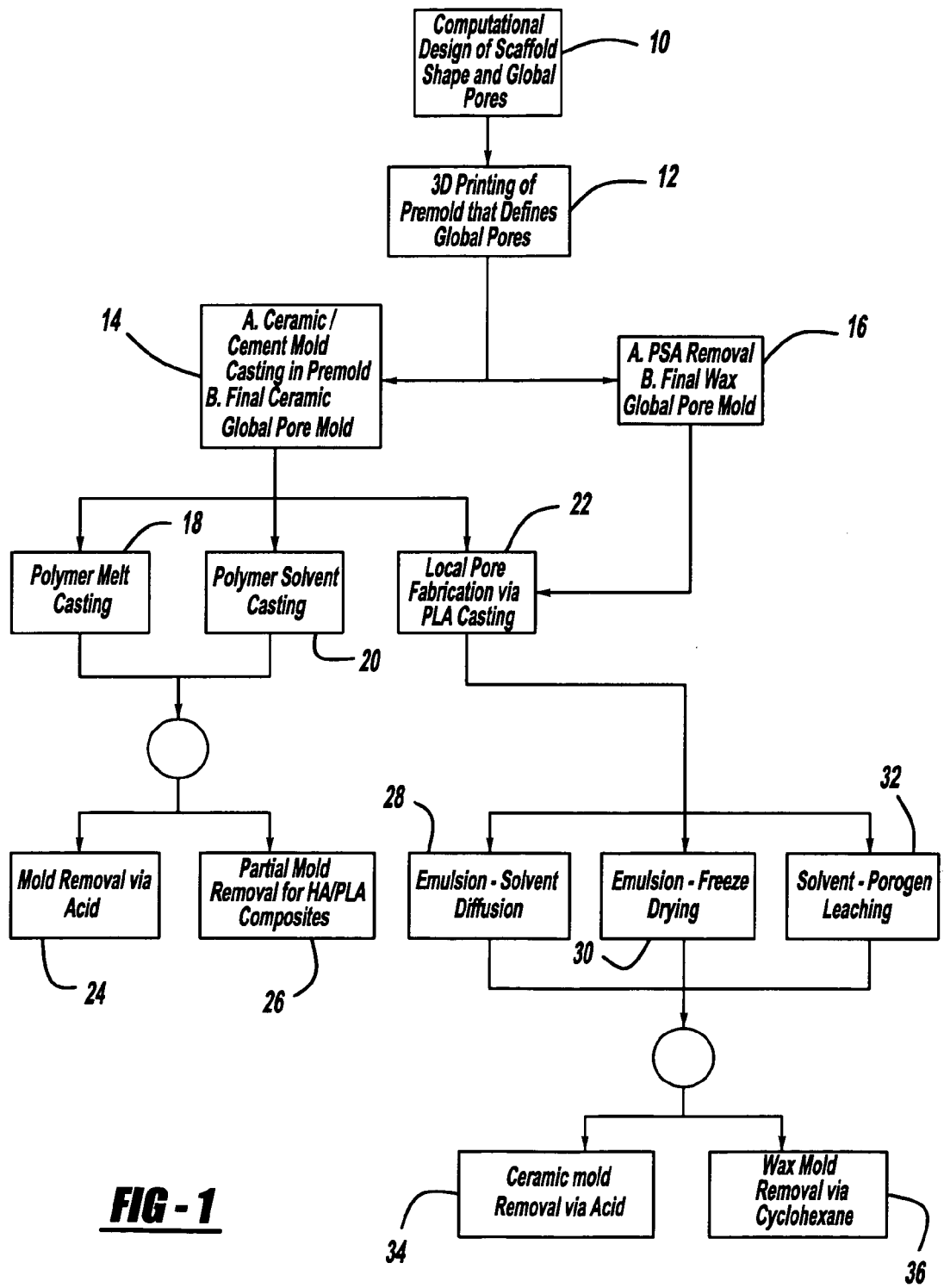
FIG. 1 is a flowchart illustrating an example of the method of the present invention.

Referring to FIG. 1, an overall description of one embodiment of the method of the present invention will be described. The methodology starts at block 10 wherein a computational design of the scaffold shape and global pores is performed. From block 10 the methodology continues to block 12. In block 12, three dimensional printing of the premold that defines the global pores is performed.

From block 12, the methodology advances to either block 14 or block 16. In block 14, the ceramic or cement mold casting is performed in the premold. Thereafter, the final ceramic global pore mold is provided. From block 14, the methodology advances to block 18, 20, or 22.

In block 18, polymer melt casting is performed. In block 20, polymer solvent casting is performed. In block 22, local pore fabrication is performed by way of PLA casting.

Referring again to block 16, in this step of the methodology PSA removal is performed. Thereafter, the final wax global pore mold is provided. From block 16, the methodology continues to block 22. As recited above, in block 22, local pore fabrication is performed by way of PLA casting.

Referring again to blocks 18 and 20, from either of these steps, the methodology advances to either block 24 or 26. In block 24, mold removal is performed by way of an acid. In block 26, partial mold removal for HA/PLA composites is performed.

Referring again to block 22, after this step, the methodology advances to either block 28, 30, or 32. In block 28, emulsion-solvent diffusion is performed. In block 30, emulsion-freeze drying is performed. In block 32, solvent-porogen leaching is performed.

From any of blocks 28, 30, and 32. The methodology advances to either block 34 or 36. In block 34, ceramic mold removal is performed via an acid. In block 36, wax mold removal is performed by way of cyclohexane.

As noted, the material type from which scaffolds are manufactured influences cell function as well as protein absorption and confirmation. One aspect through which materials can regulate cell function is via material surface properties that may include hydrophilicity, zeta potential, charge, and roughness. Additional control is afforded by post modification of these surfaces. Cell culture surfaces may be coated with ligands that modulate cell functions including cell attachment, spreading, proliferation, differentiation, and synthesis of secreted cell products including extracellular matrix. Post modification of surfaces may also be used to tether desirable compounds, including viral particles and drugs for delivery to cells, and enzymes and/or catalysts for chemical reactions. These modifications are referred to as functionalization of the material surface. Several functionalization methods are applicable to the materials manufactured using the disclosed fabrication methods. The functionalization methods of the present invention are more stable than current state of the are because they inhibit thermodynamically driven detachment from and internalization into the material of the tethered substances.

The method of the present invention will now be described in greater detail. In the first step, the computational design of the desired structure is performed. The external scaffold design and global pores (macro-porous architecture) can be created using either traditional computer aided design (CAD) techniques that are computational geometry based or a newly developed image-based design (IBD) technique whose details are fully described in co-pending patent application Ser. No. 10/178,419 entitled DESIGN METHODOLOGY FOR TISSUE ENGINEERING SCAFFOLDS AND BIOMATERIAL IMPLANTS to Hollister et al. which is expressly incorporated by reference herein. The IBD methods allow design of complex internal porosity (including pore geometry, orientation, interconnectivity, and branching) and of scaffold external shape to match implant site requirements using a patient specific image.

Scaffold designs can also be generated using commercial CAD software, but integration of scaffold design with imaging data and creation of complex porosity is not optimized.

IBD or CAD created mold designs are saved either as stereolithography triangular facet data (*.stl), stereolithography contour data (*.slc) or SolidScape contour data (*.slf) and are then converted to appropriate input files for computer aided manufacturing (CAM) using commercial software for 3D printing (e.g., ModelWorks, Solidscape, Inc) and stereolithography (e.g., 3D Lightyear, 3D Systems).

Figure 2:
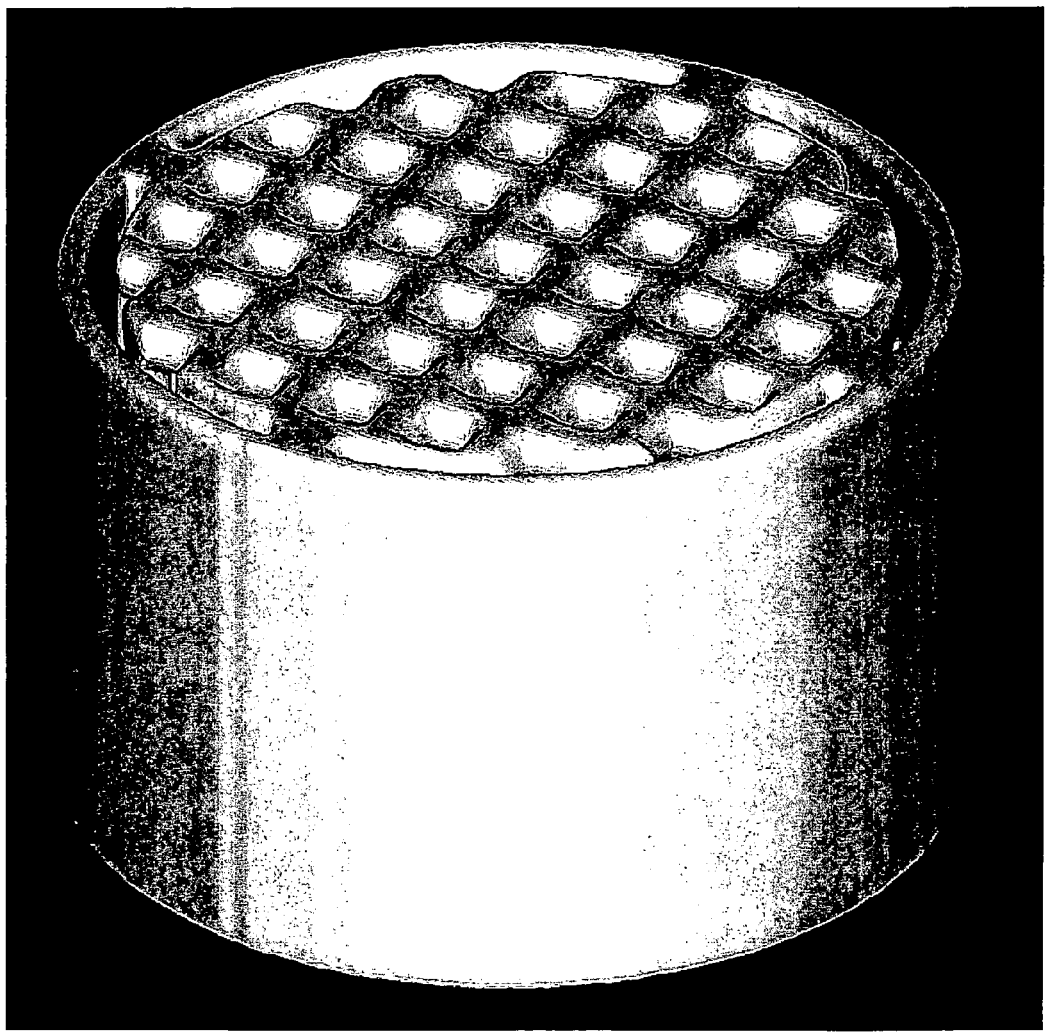
FIG. 2 shows an imaged-based design (IBD) mold for scaffold casting (solid regions define the final global pores, 600 μm orthogonal cylindrical channels that are spaced 500 μm apart)

In an experimental run of the present invention, the external scaffold shape and global-porous architecture were designed using an image based design (IBD) method. Orthogonally pored scaffold designs were 8 mm diameter by 8 mm height cylinders with either square or circular equi-spaced, orthogonally branching and interconnected global pores channels (global pore volume fraction =50%, FIG. 2). Trabecular bone biomimetic scaffold designs possessed the same cylindrical external geometry. However, the internal structure was defined using human distal femoral bone computed tomography (CT) data at double scale. Designs defined by image data were converted into STL data using Imagedes (Voxel Computing, Inc., Ann Arbor, Mich.), imported into Modelworks software (SolidScape, Inc., Merrimack, N.H.), and converted into input files for 3D printing.

The second step of the method of the present invention involves mold fabrication. The casting methods allow fabrication of complex global porosity (including pore geometry, orientation, interconnectivity, and branching), of varied local pores, and of scaffold external shape to match implant site requirements. Molds for casting the designed scaffold are fabricated using direct deposition of the mold material, preferably by using 3D printing. Several other SFF technologies can be used to fabricate molds, including fused deposition (FDM), selective laser sintering (SLS), direct material deposition (DMD), stereolithography (STL), layered object manufacturing (LOM), and 3D printing of binders or solvents on powdered material beds (3DP).

Molds can be fabricated from waxes (any of various natural, oily or greasy heat-sensitive substances, consisting of hydrocarbons or esters of fatty acids that are insoluble in water but soluble in several organic solvents), plastics (any of various organic compounds produced by polymerization), sugars (any of a class of water-soluble crystalline carbohydrates), ceramics (any of various hard, brittle, heat-resistant and corrosion-resistant materials made by shaping and then firing a mineral composition at a high temperature), and cements (any of building materials that form a paste when mixed with water and harden into a solid).

The useful properties of these materials in casting are as follows. Waxes (e.g. paraffin and beeswax) and plastics (thermosetting and thermoplastic, e.g. polysulphonamide, polystyrene, polyesters, silicones) are combustible and/or meltable, and soluble in organic solvents. As such, wax and plastic molds can be removed by using solvents and heating temperatures exclusive for the cast material. Sugars (e.g. starch, cellulose, and saccharides) are water-soluble. As such, sugar molds can be removed by soaking in water and other hydrated solvents. Cements and ceramics (e.g. plaster of Paris, hydroxyapatite) are dissolvable and breakable but can withstand high temperatures and pressures. As such, cement and ceramic molds can be used for injection molding and melt processing.

Figure 3:
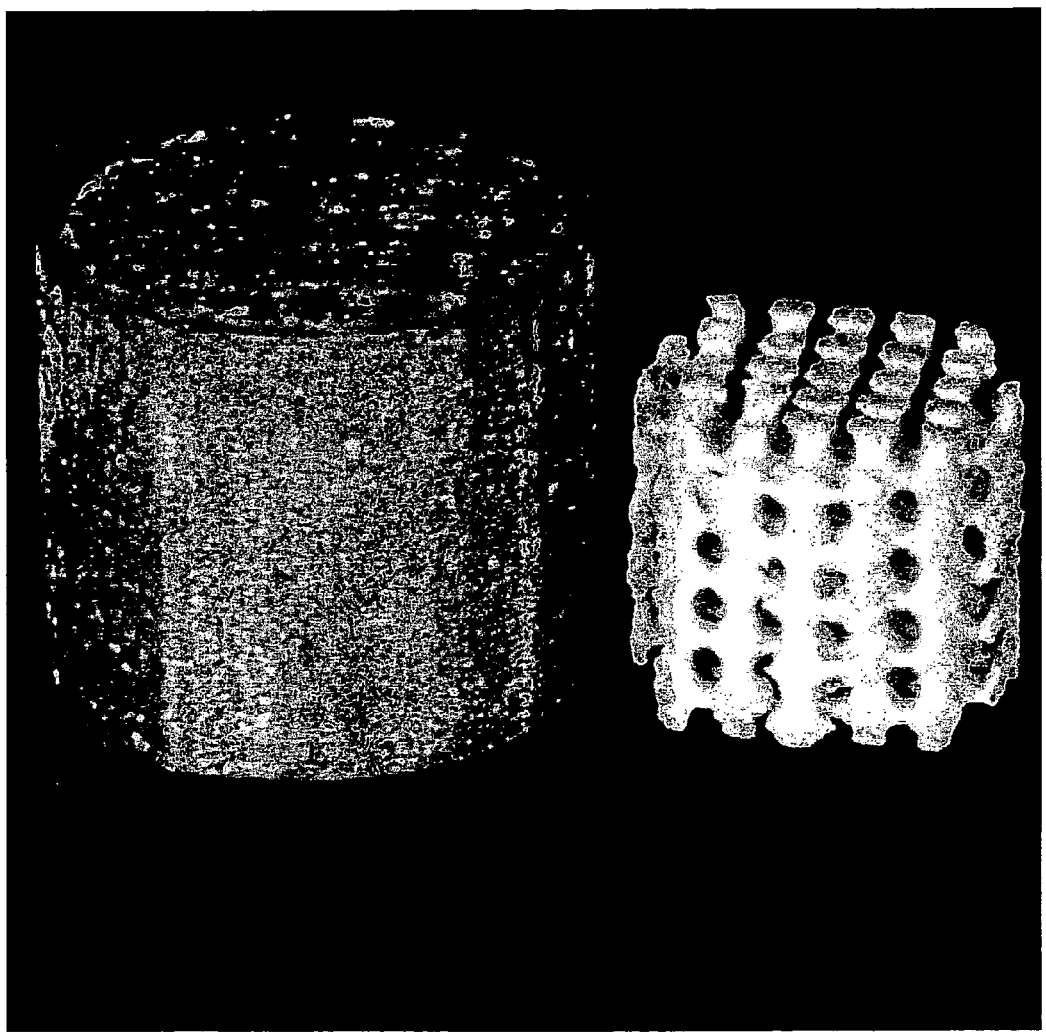
FIG. 3 shows an indirect wax mold on the left fabricated on a SolidScape MM2 3D printer and a cast ceramic mold on the right for polymer/ceramic biphasic scaffold fabrication (the ceramic pores define the polymer struts to be cast)

In the preferred method, wax or polysulphonamide molds are created using a SolidScape, Inc. (Merrimack, N.H.) Model Maker II 3D printer (FIG. 3). The printer deposited molten PSA followed by molten wax to make one layer of the mold. The process was repeated in a layer-by-layer fashion. After printing, the PSA molds were obtained by melting the wax and dissolving residual wax in Bioact. Wax molds were obtained by dissolving the PSA in acetone or dimethylsulfoxide.

Cement molds are created by casting cement in an inverse mold made of wax or polysulphonamide fabricated on a Model Maker II printer. A final cement mold is made by removing the inverse mold via solvation or heating. Ceramic molds are created by casting a ceramic/binder (HA and acrylic) slurry in an inverse mold made of wax or polysulphonamide or by casting in an inverse mold made of epoxy resin (or other stereolithographic resin) (SL 5170, Vantico, Inc. Basel, Switzerland) fabricated using a 3D Systems (Valencia, Calif.) SLA 250 System.

In a preferred method, ceramic molds or scaffolds are created by casting a low-viscosity ceramic slurry made of tricalcium phosphate (TCP) powder, acrylates, dispersants, and initiators. The particle size of the TCP powder should be below 100 microns to allow final sintering, preferably lower than 30 microns. The viscosity of the acrylates should be lower than 100 mPa·S to ensure a low viscosity of the final slurry. The dispersants can be either anionic or cationic dispersant, preferably a mixture of the two. The initiator should allow the curing process to take place below the melting point of the wax mold, preferably the peroxide derivatives or similar. In particular, the a preferred formulation is comprised of 40 volume percent of tricalcium phosphate powder in the size of 1 micron in diameter. The balancing reactive medium is a 50:50 mixture of isobornyl acrylate and propoxylated neopentyl diacylate. The ceramic powder is dispersed with 2.5% of a cationic dispersant (a polypropopoxy quaternium ammonium acetate) and 2.5% of an antionic dispersant (an aromatic phosphate ester). The particular formulation exhibits a Newtonian viscosity of 23 Pa·S at a shear rate of 10 sec$^{-1}$, a particular flow behavior appropriate for casting in the molds. A thermal initiator, benzoyl peroxide is added to the slurry just prior to casting. The thermal initiation mechanism employed in this disclosure for this ceramic slurry is different from prior art initiation mechanisms. An accelerator, N,N-dimethyl p-toludine, is added to the slurry to allow the initiation of the curing reaction at room temperature, below the melting point of the wax mold. The addition of the N,N-dimethyl p-toludine eliminates the need to heat the mold to 80° C. to initiate the reaction. After curing. the cured ceramic slurry is heat-treated to 1150° C. to remove the cured acrylates and to sinter the TCP powder.

Preferably, cast ceramic molds are subject to a burn out cycle that removes organic binders and the inverse mold. The ceramic pre-mold is then sintered (at about 1300° C. maximum) yielding the final ceramic mold.

In the third step of the method of the present invention, the material selected for the structure to be formed is cast in the mold. The method of the present invention enables novel 3D scaffold fabrication from diverse materials with controlled local/global-porous architectures because the structures are created by casting in IBD or CAD/CAM designed and manufactured molds. These casting techniques allow for the fabrication of scaffolds from more materials than possible with direct SFF techniques. Furthermore, by employing mold materials that shrink during curing or burnout, scaffolds with global pores smaller than the minimum feature size of current direct SFF manufacturing methods can be fabricated.

Advantageously, the material chemistry need not be altered for manufacturing compatibility. Additionally, both solution and molten processing of the material is possible with these casting methods. Most conventional local-pore polymer processing techniques are also compatible with these methods. Local-pore manufacturing methods may be enhanced with an annealing step after polymer casting in order to fuse polymer particles together and increase scaffold mechanical integrity. Coupled with the high-resolution control of global-pore structure dictated by the mold design, controlled local/global-pore internal architecture is possible within one structure. As with other SFF techniques, external scaffold geometry can also be controlled.

The following several paragraphs describe a few casting processes suitable for use in the method of the present invention. The steps for some processes are illustrated through reference to their respective block numbers from one example of the embodied methodology in FIG. 1. All methods utilized steps in Blocks 10 and 12.

First, a process for solvent casting in wax and plastic will be described. Particular plastics are compatible with casting in select waxes and plastics. For example, polymers of α-hydroxyacids and urethane can be solubilized in organic solvents and cast in wax molds. Micro-porosity is created by using any conventional technique. Polylactide (PLLA or PLA) and copolymers of polylactide and polyglycolide (PLGA) are dissolved in methylene chloride. Polyglycolide (PGA) is dissolved in 1,1,1,3,3,3-hexafluoro-2-propanol.

Second, a process for solvent casting in ceramic and cement will be described. Plastics solubilized in solvents that dissolve wax and plastic molds can be cast in ceramic and cement molds (FIG. 1, Block 14). Micro-porosity is created by using any conventional technique (FIG. 1, Block 22). In order to create scaffolds with no micro-porosity, the solubilized plastic is poured into the mold and the solvent evaporated under atmospheric pressure or a vacuum (FIG. 1, Block 20). The process is repeated until the solubilized plastic no longer infiltrates the mold.

Figure 4:
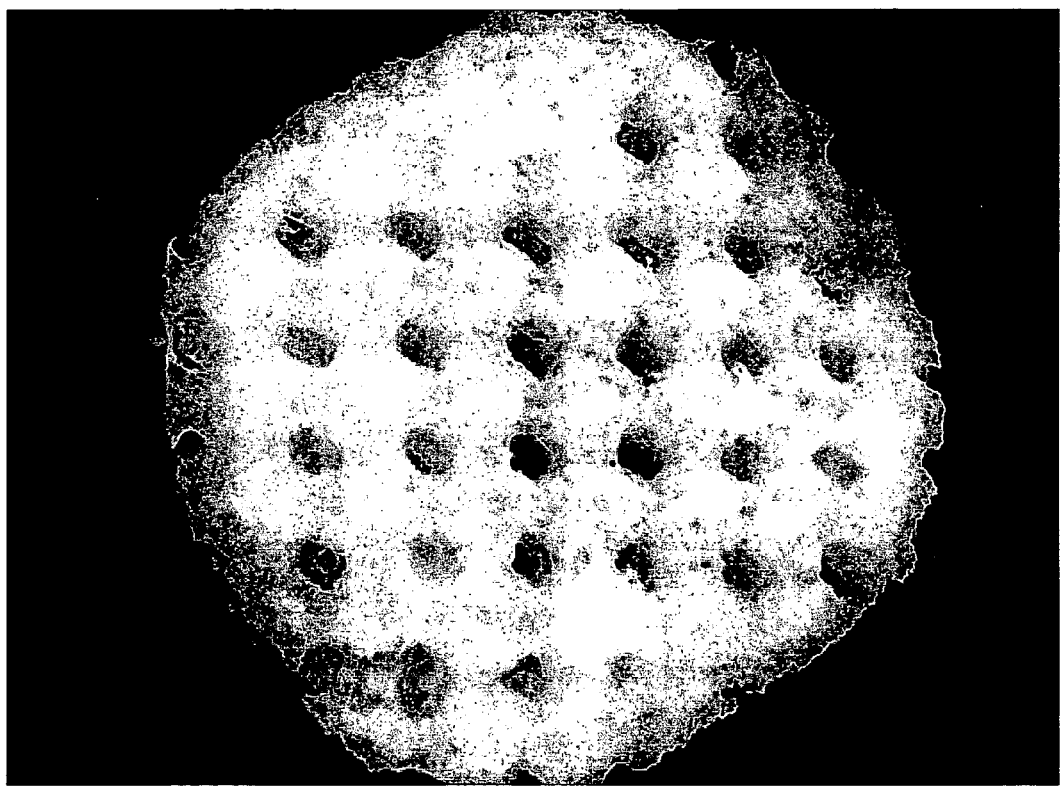
FIG. 4 shows salt leaching fabricated globally and locally porous PLA scaffold, 8 mm diameter×8 mm height (scaffolds shrank during drying); 100% PLLA polymer cast in chloroform solvent FIG. 5 (a higher magnification image of FIG. 4) shows an 18.4×SEM of 600 μm diameter designed orthogonal interconnected global pores.
Figure 5:
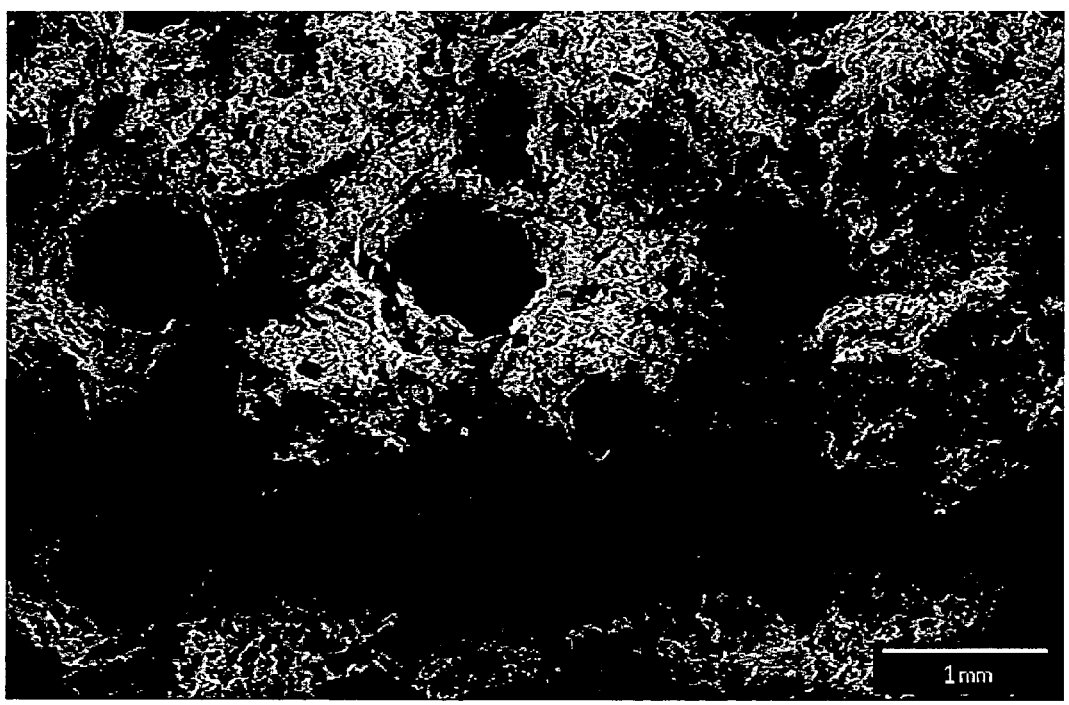
Figure 6:
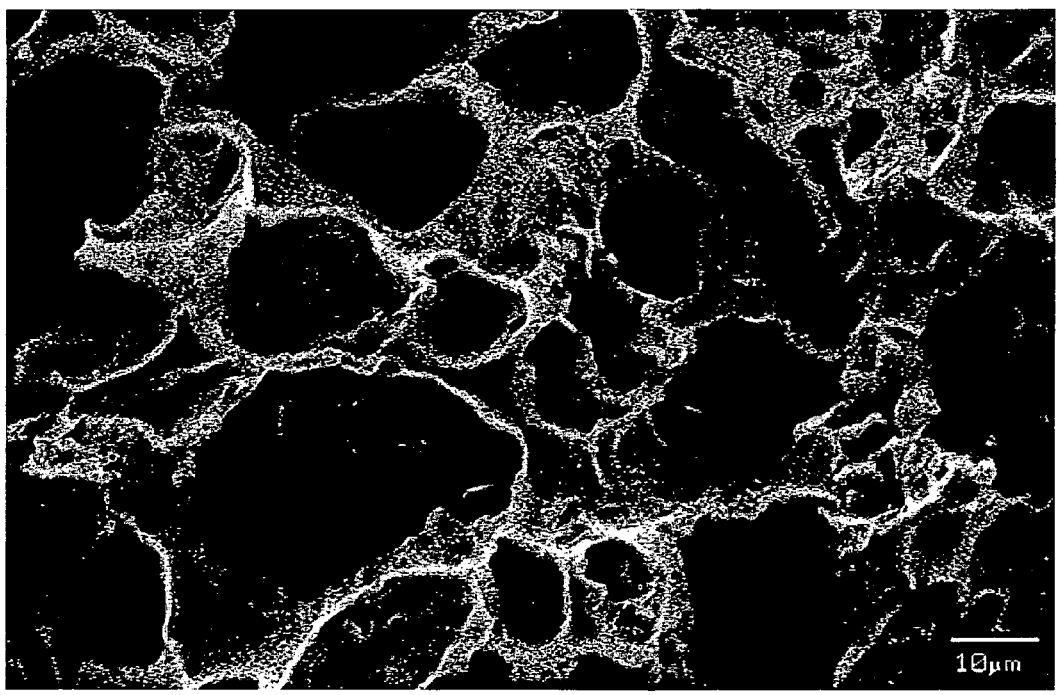
FIG. 6 (a higher magnification image of FIG. 4) shows a 1,020×SEM of 50–100 μm wide randomly interconnected local pores defined by NaCl salt porogen.
Figure 7:
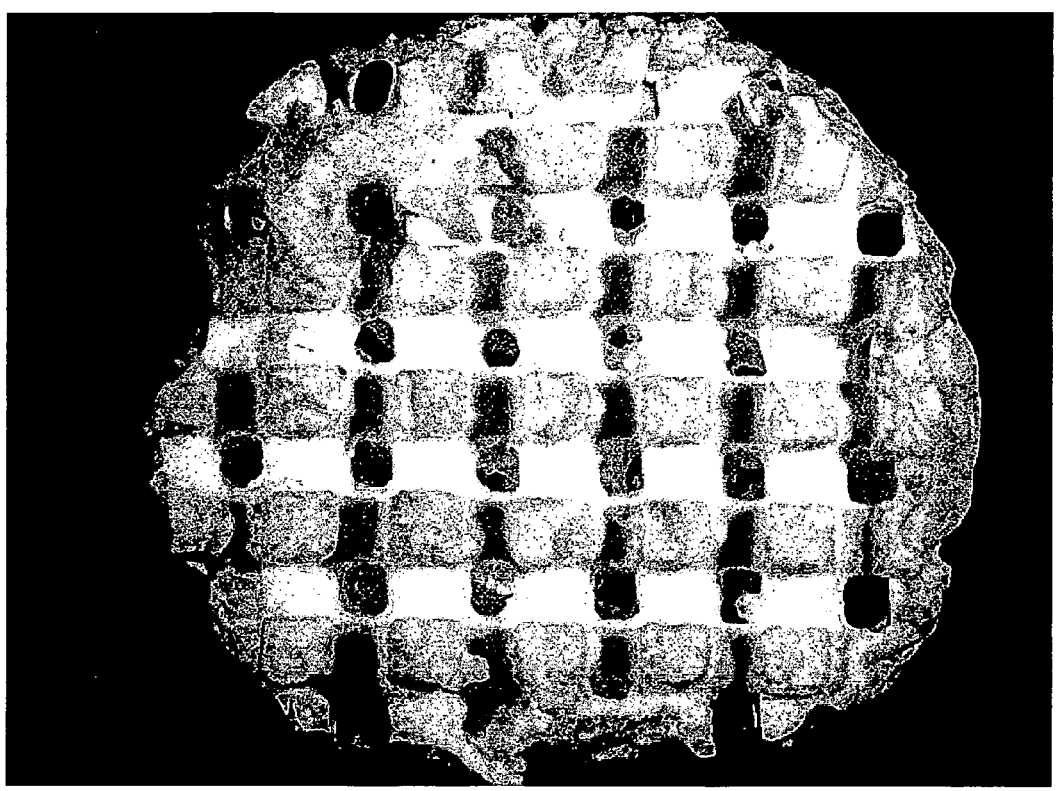
FIG. 7 shows an emulsion-solvent diffusion fabricated globally and locally porous PLA scaffold, 8 mm diameter ×8 mm height; 100% PLLA polymer cast in tetrahydrofuran solvent FIG. 8 (a higher magnification image of FIG. 7) shows a 36.8×SEM of 600 μm rectangular orthogonal global pores (the horizontal ridges (arrows) on global pore channels and strut surfaces are produced by the 3DP layered mold manufacturing, fracturing the scaffold in half for imaging revealed the internal local pores (F, top))
Figure 8:
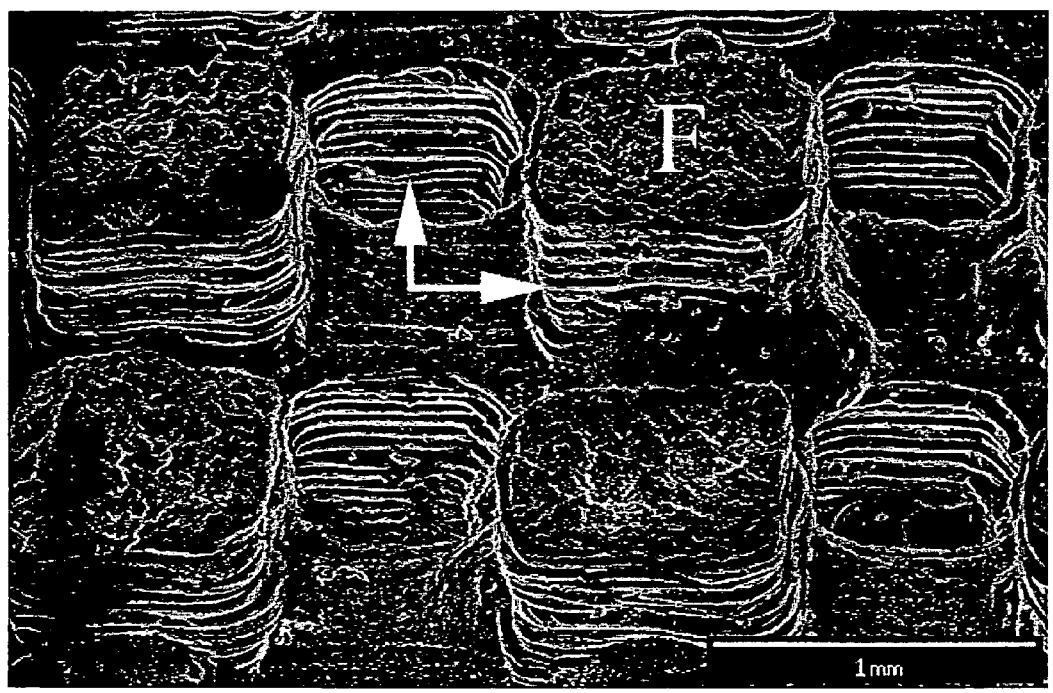
Figure 9:
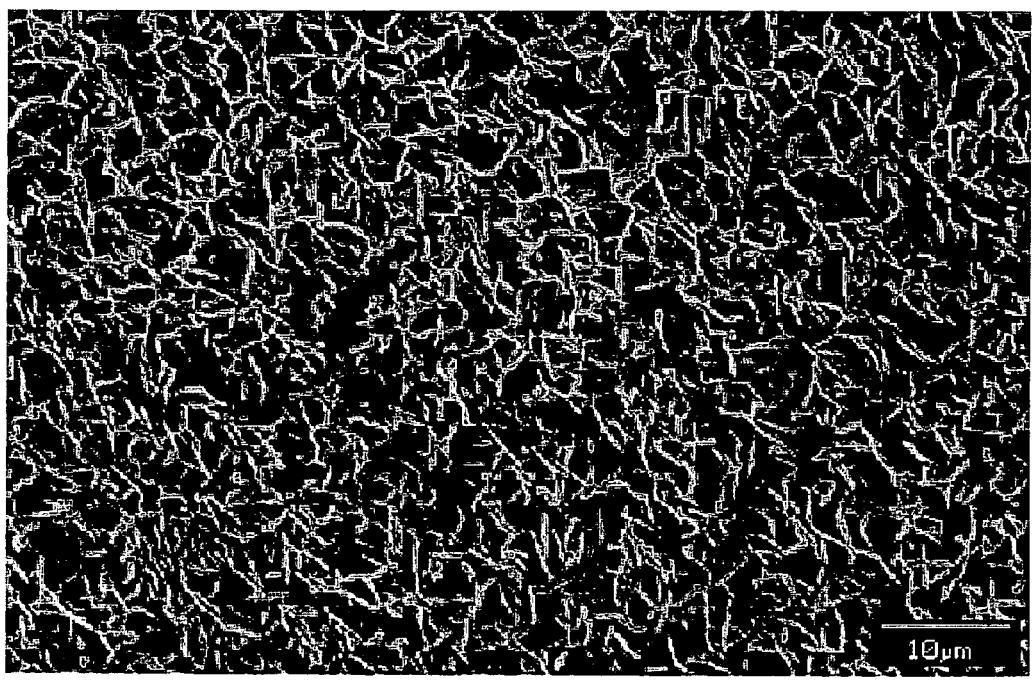
FIG. 9 (a higher magnification image of FIG. 7) shows a 2,400×SEM of local porosity consisting of interconnected plate structures (7×5 μm average) yielding 5–11 μm void openings (the internal local pores do not have ridges)

An example of solvent casting in ceramic will now be made with reference to FIGS. 4–9. FIGS. 4–6 show 100% PLLA orthogonal global-pore scaffolds with local-porous structure created using porogen leaching (FIG. 1, Blocks 14,22,32,34). FIGS. 7–9 show 100% PLLA orthogonal global-pore scaffolds with local-porous structure created using emulsion solvent diffusion techniques (FIG. 1, Blocks 14,22,30,34). The scaffolds shown in FIGS. 4–9 include two concurrent orders of internal architecture, a designed global pore lattice ($\leq 100$ μm feature size) that is interconnected a priori on a global scale and a local pore architecture (5–100 μm feature size, note feature size comments in the brief description of the drawings) that is interconnected within local regions of the scaffold microstructure.

Scaffolds containing local pores were made using several methods. For porogen leaching, 104–124 μm sieved NaCl grains were packed into ceramic molds and cast with 7.5% w/v PLA in chloroform. Solvent was evaporated under 15"Hg vacuum overnight (FIG. 1, Block 32). For emulsions, a saturated PLA in tetrahydrofuran emulsion (60° C.) was cast and molds cooled to room temperature (22.5° C.), soaked in ethanol for two days, and air dried overnight (FIG. 1, Block 28). Finer plate local pore structures were created by snap freezing cast molds in liquid nitrogen and freeze drying under a dry ice and ethanol slurry at 30"Hg vacuum (FIG. 1, Block 30).

Third, a process for casting uncured material in wax and plastic will be described. Materials that cure without heat generation or that are modestly exothermic upon curing may be cast in wax and plastic molds. Silicone elastomer (Sylgard 184, Dow Corning Corp, Midland, Mich.) may be cast and cured in wax and polysulphonamide molds. After casting, the elastomer is preferably placed in a 37° C. oven to speed curing over 12 hrs.

Fourth, a process for casting uncured material in ceramic and cement will be described. Materials that are exothermic upon curing may be cast in ceramic and cement, including poly(methylmethacrylate) and commercial bone cements.

Fifth, a process for melt casting in ceramics will be described. Ceramic and cement molds enable melt processing of plastic scaffolds. PLLA, PLGA, PGA, and polyurethane (PU) scaffolds have been manufactured using this method. Ceramic molds are heated in an oven set to 10–20° C. above the plastic melting point ($T_m$) (PLA $T_m$=120° C., PGA $T_m$=150° C.). Molten polymer is allowed to flow into the mold. The molten polymer/molds are then subject to a vacuum while heated in order to remove any air from the mold and melt (FIG. 1, Blocks 14, 19, 24).

Figure 10:
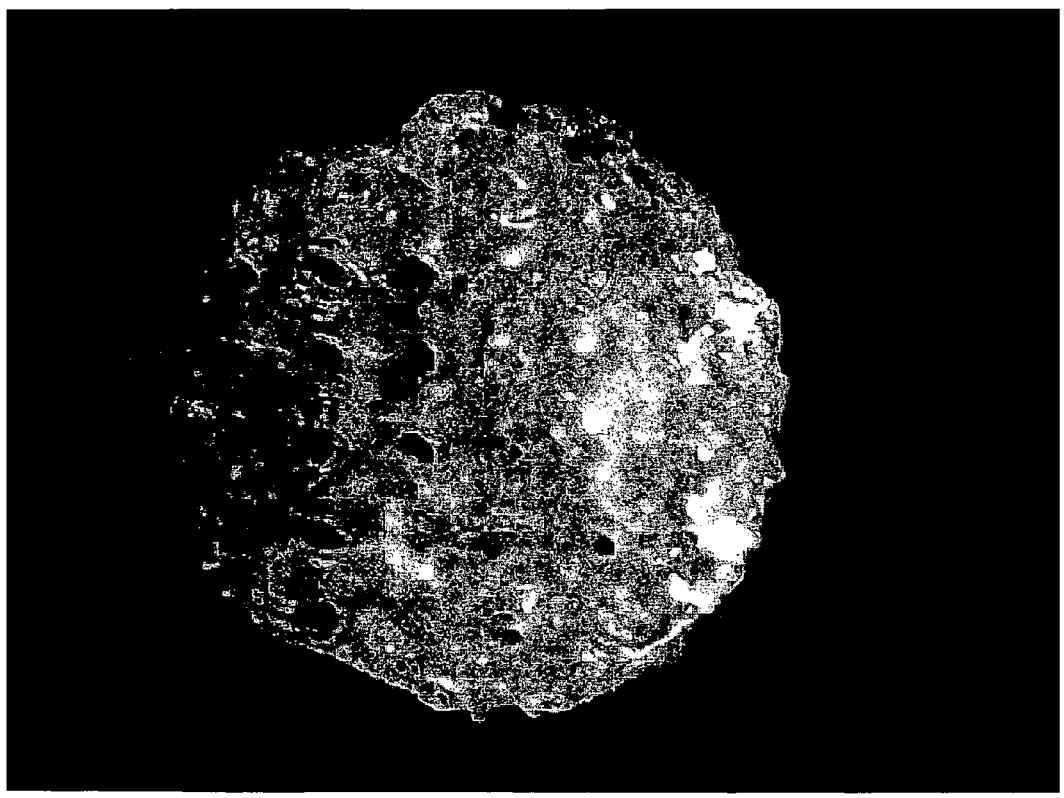
FIG. 10 is a photograph of macroscopic architecture of 4 mm diameter polyurethane (PU) scaffold constructed using melt casting.
Figure 11:
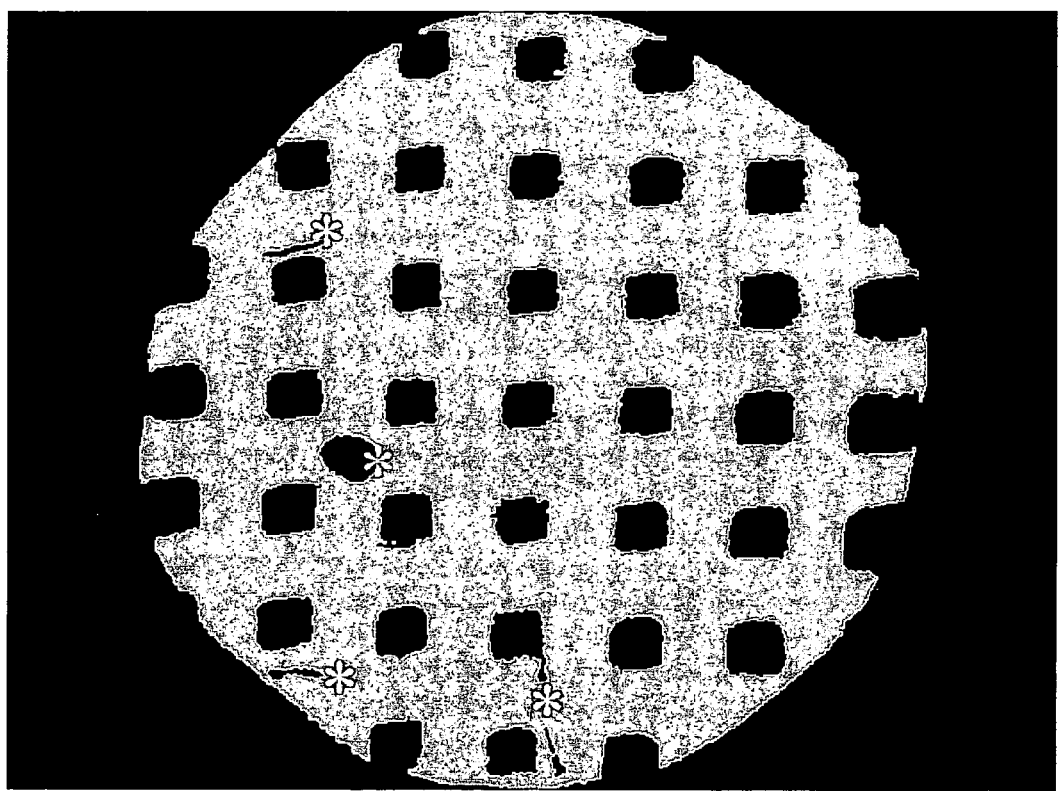
FIG. 11 shows a micro-CT slice of global-porous PLA scaffold melt cast in a ceramic mold (small voids produced by air bubbles are present in the lower and left regions (*))
Figure 12:
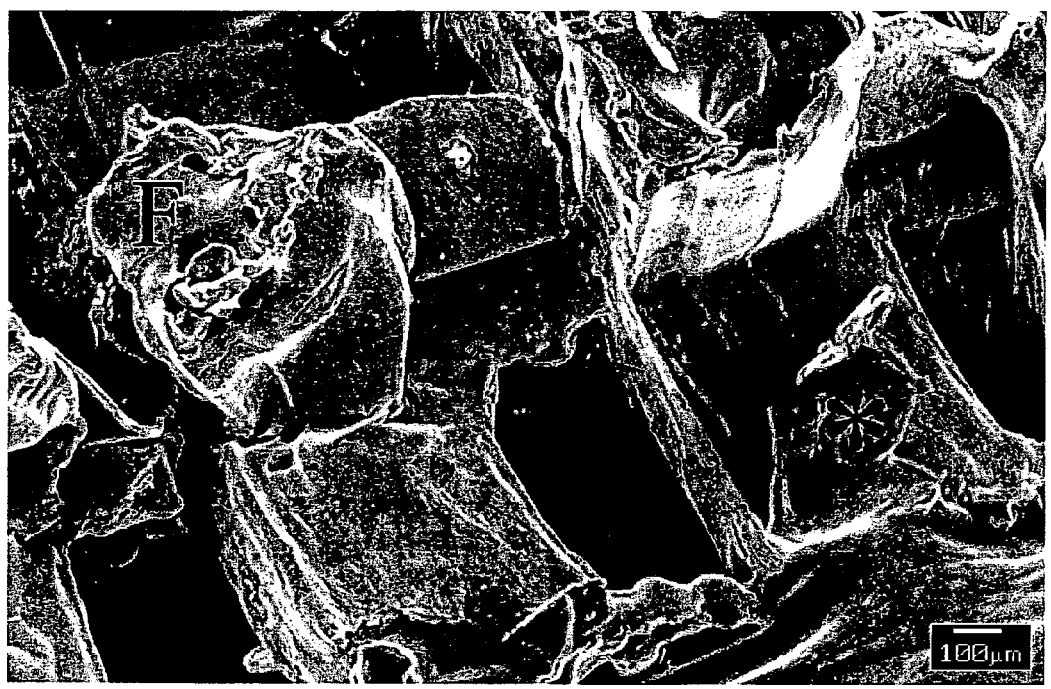
FIG. 12 (a higher magnification image of FIG. 11) shows a 57×SEM of 500 μm rectangular strut architecture (the small protruding piece of PLA (*, bottom right) was produced by a crack in the mold, the rough strut surfaces (F, top) are the result of fracturing the scaffold in half for imaging)
Figure 13:
FIG. 13 (a higher magnification image of FIG. 11) shows a 130×SEM of a smooth strut surface with one thin furrow caused by the mold.

An example of a process for melt casting in ceramics will now be described with reference to FIGS. 10–13. FIG. 10 shows the result of casting PU in ceramic molds. In FIGS. 11–13, a 100% PLLA, scaffold was created containing 3D, orthogonal, interconnected, 90° branching, rectangular global struts. Melt casting allows the inclusion of micro-pores using porogen leaching techniques. For example, a salt packed ceramic mold may be used. However, infiltration of molten polymer is slow and requires prolonged heating and a vacuum. These may damage the cast plastic. To overcome this limitation, injection molding may be used.

Sixth, a process for injection molding in ceramics will be described. Ceramic and cement molds of designed macroporosity may be used for injection molding of plastics in melt or uncured forms. Injection molding facilitates material infiltration into the mold, as the material can be processed under high temperatures and pressures. Molds should be places in dies that mount within conventional injection molding devices. These dies may be manufactured to fit external mold shape or the molds may be manufactured with extra material so they fit within standard dies.

Since local injection molding utilizes pressure above atmosphere and no material solvents, most conventional micro-pore inclusion methods should not be used. However, suitable porogens can be included as in melt casting. The porogens are then leached out of the final material.

Seventh, a process for composite material casting will be described. Composite materials may be manufactured using several methods. As used herein, a composite means a structure composed of two or more materials that have different chemical structures or a structure composed of the same material but with differing spatial density or molecular weight distributions. The materials composing a composite may occupy the same volume as a blend, occupy different volumes of one structure as in a discrete composite, or may be combinations thereof.

Blend (ceramic or cement)/plastic composites are manufactured by melt or solution casting of plastics containing ceramic particles of desired size and geometry. HA/PLLA blend composites with designed macro-porosity have been manufactured using melt processing.

Non-blend composites with discrete regions of differing plastics can also be manufactured using solvent and melt processing. In this case, the molds are designed to contain two or more exclusive pore or lattice networks. One plastic is cast per network, interdigitation of the differing plastics is controlled by the mold structure and by using plastics with exclusive solvents, by casting plastics to controlled depths within the mold, or by selectively removing part of the mold before casting subsequent plastics. Exclusive solvents are those that will dissolve one set of the desired materials but not the other sets.

Further, non-blend composites with discrete plastic and ceramic/cement regions that are mechanically interdigitated can be manufactured using solvent and melt processing. The methods for fabricating these structure may also be used to fabricate discrete composites from metals, plastic, polymers, ceramics, and cements. Three methods are preferred to create non-blend (ceramic or cement)/plastic composites.

In the first method, the ceramic or cement scaffold is created using slurry casting. Then a wax or plastic mold is built upon the ceramic/cement base structure. This mold is used to cast the plastic or to cast a second ceramic/cement mold. This second ceramic/cement mold is of different solubility than the scaffold on which it is constructed. For example, a plaster of Paris mold may be built on a HA scaffold. The desired plastic is melt or solvent cast into the secondary mold and into regions of the base ceramic/cement scaffold that have been designed with pores for plastic infiltration and mechanical interdigitation of the plastic region with the ceramic/cement region. The secondary mold is then melted or dissolved away. This method uses two or more molds, one mold to create the base ceramic/cement scaffold and the other secondary molds build upon the ceramic/cement scaffold for plastic casting. This method provides for fine interdigitation control.

Figure 14:
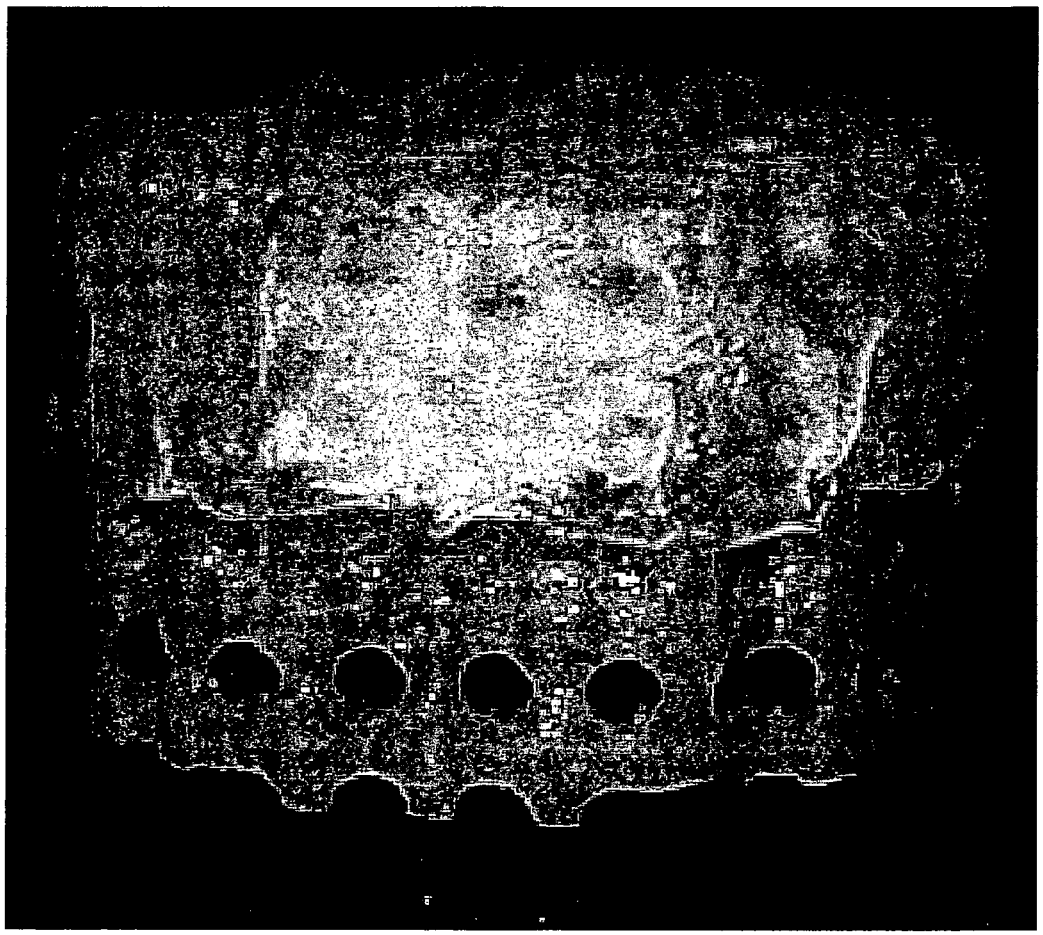
FIG. 14 shows a biphasic PLA/HA ceramic scaffold (PLA global pores are 600 μm diameter, HA global pores are 500 μm)
Figure 15:
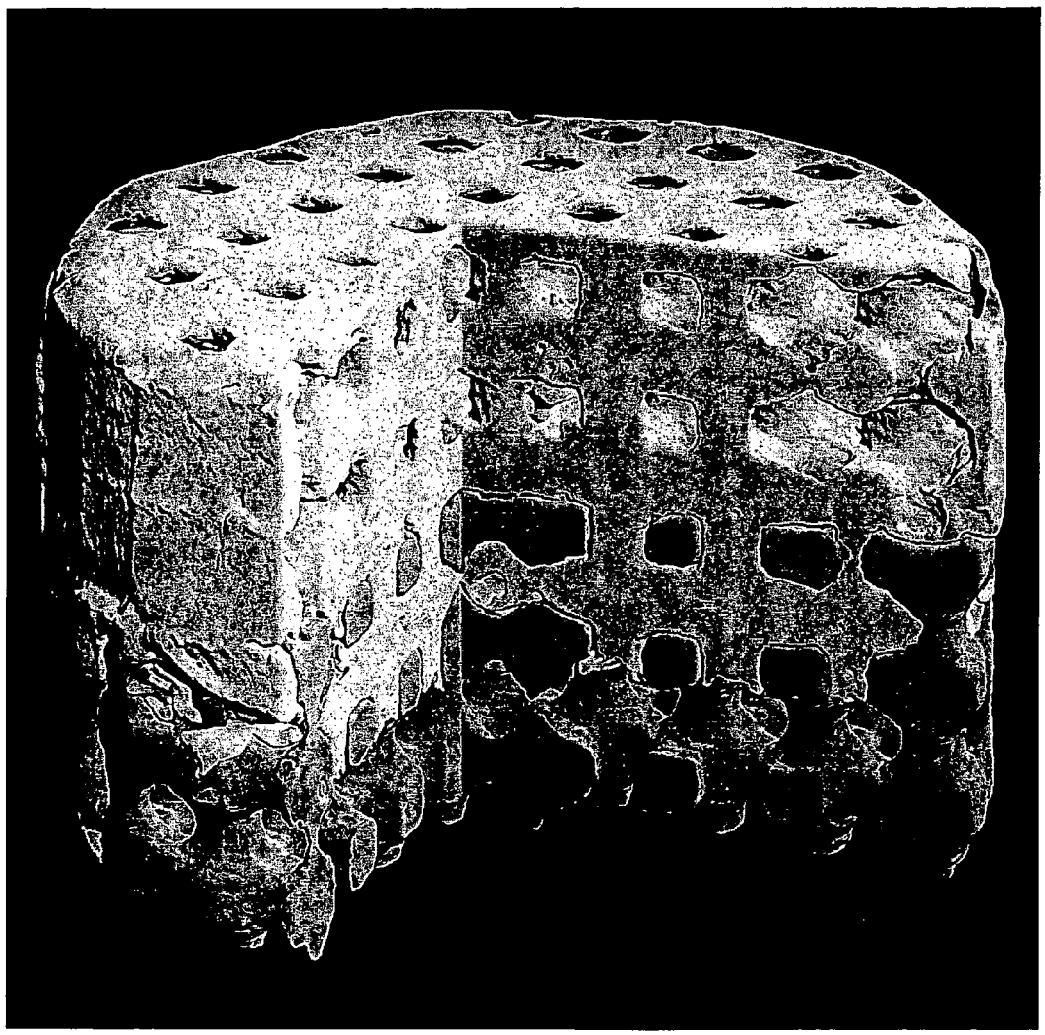
FIG. 15 shows a μCT of the biphasic scaffold in FIG. 14 with a portion cut away to depict interdigitation of both phases (the cut is at an angle to pore lattice to simultaneously view pore structure and material struts, curved surfaces at polymer/ceramic interfaces are an artifact of image processing, PLA is in direct contact with HA)
Figure 16:
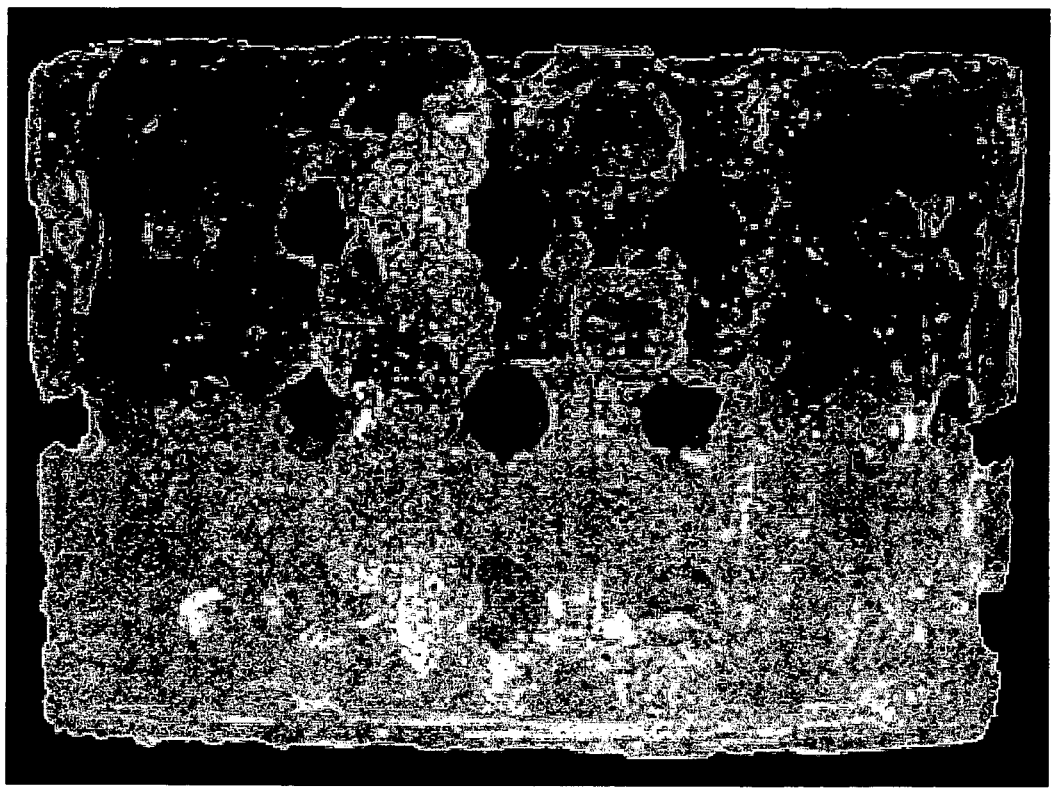
FIG. 16 shows a biphasic PLA/PGA scaffold, 8 mm diameter ×8 mm height, with orthogonal 800 μm diameter pores (top & dark =PGA, bottom & light=PLA)
Figure 17:
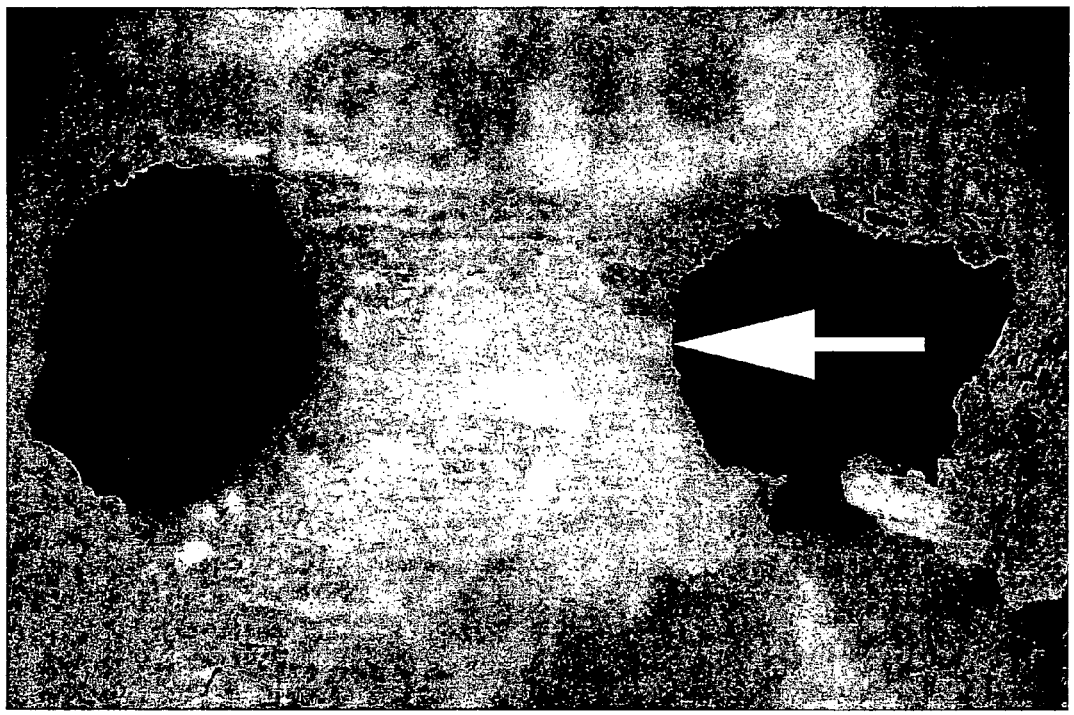
FIG. 17 (a higher magnification image of FIG. 16) shows an interface between PGA and PLA at a pore wall (arrow) (PGA is above the arrow, PLA below, the horizontal ridges along the wall are produced by the 3DP layered mold manufacturing)
Figure 18:
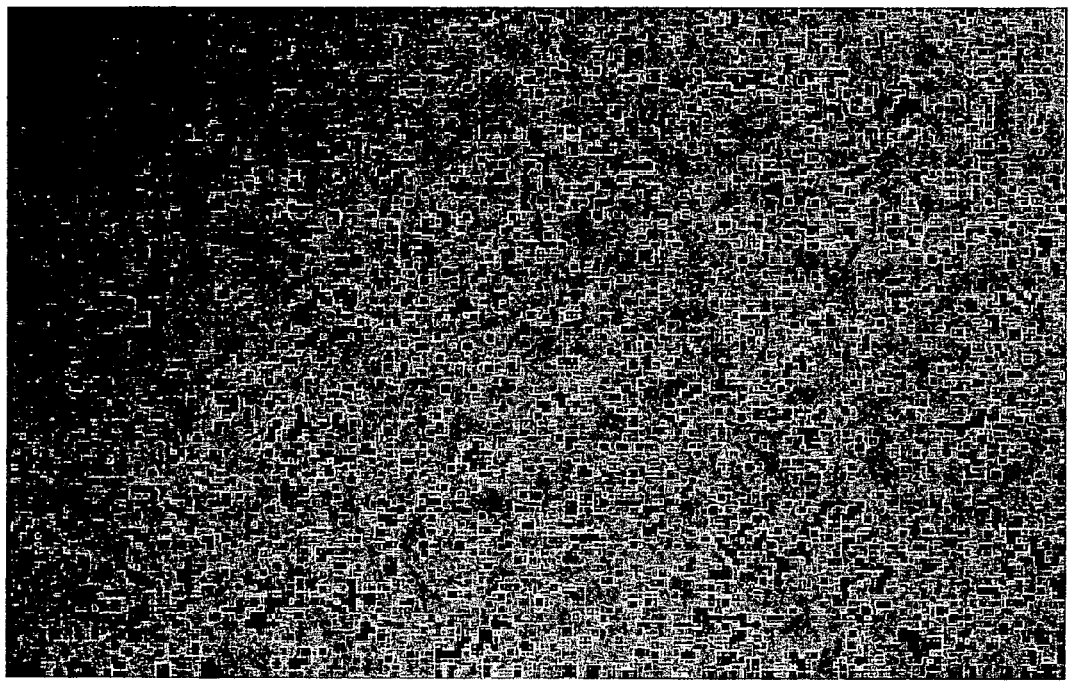
FIG. 18 shows cell adhesion and spreading on fibronectin coated Sylgard after 1 hr. (cells were allowed to adhere over 1 hr and then the surface was rinsed, only adherent cells remained)

In the second non-blend composite manufacturing method, only one ceramic/cement scaffold is used. This structure is created with additional porous or lattice networks that serve as the mold for the plastics to be cast. The additional networks may not be continuous with other pore networks within the ceramic/cement scaffold. This facilitates plastic melt or solution casting of the desired plastic structure without blockage of other pore networks within the ceramic/cement region. Ceramic/cement free regions of the scaffold are then created by selective application of ceramic/cement solvents. An HA/PLLA composite scaffold has been created with the second method. An example of such a composite scaffold is shown in FIGS. 14–15. A PLA/PGA composite scaffold has been created with the second method and is shown in FIGS. 16–17. This method provides for fine interdigitation control while using only one mold.

In the third method, polymer ceramic composites are made by assembly of the polymer and ceramic regions. The ceramic is heated and the polymer pressed onto the ceramic. The polymer melts into the anchor pores in the ceramic, locking the two phases together. The polymer also may be fused to the ceramic via the use of polymer solvents. This procedure provided course control of interdigitation. The benefits of this method is that it avoids exposure of the polymer phase to ceramic solvents Two examples of processes for discrete composite manufacturing will now be detailed with references to FIG. 14–17.

Polymer discrete composite PLA/PGA scaffolds were made with a two part casting process (FIG. 16, 17). The mold was first placed into a reservoir containing molten PGA. The reservoir level controlled the desired PGA infiltration depth into the mold. The PGA level and casting time were adjusted to compensate for mold displacement of polymer and capillary action of PGA up the mold pores. After PGA infiltration, the partially cast mold was cooled to 130° C. and PLA cast, thereby physically bonding the materials. Cast molds were cooled and maintained at 100° C. for 30 minutes to allow polymer crystal formation (FIG. 1, Blocks 14, 18, 24).

Ceramic/polymer discrete composites were made with a casting and etching process (FIG. 14, 15). A sintered HA ceramic scaffold base was fabricated containing a primary and secondary pore network. The primary network was designed for tissue growth into the ceramic while the secondary network served as the polymer mold. The secondary network was contiguous with the primary pore network in the manufactured scaffolds. However, discontinuous networks may be manufactured, providing for polymer melt or solvent casting without blockage of primary ceramic pore networks. PLA was melt cast into half of the base as outlined in the global pore melt casting techniques. Ceramic-free regions within the scaffold were created by selective application of a ceramic solvent, yielding a non-blend, discrete composite with mechanical interdigitation of the ceramic and polymer phases (see mold removal below) (FIG. 1, Blocks 14, 18, 24).

The fourth step of the method of the present invention involves mold removal. There are three preferred techniques to separate molds from the desired cast structure. The following lists compatible methods for varied casting techniques.

First, a process for fracturing the mold could be used. This method is adequate for scaffolds of limited internal architectures.

Second, a process for melting wax and plastic molds could be used. Molds can be melted away from cast material if the melting point of the mold material is lower than that of the cast material. For example, the preferred polysulphonamide melts between 95–107° C. while the preferred wax melts between 50–75° C. Wax molds may be removed by melting in an oven at 85° C. for one hour (PSA $T_m$=95–107° C., Wax $T_m$=50–75° C.). Residual wax may be removed by washing in cyclohexane for one hour and air drying.

Third, a process for dissolving wax, plastic, ceramic, and cement molds could be used. Wax, plastic, ceramic, and cement molds can be dissolved away from the cast material. The choice of solvent depends on the mold and cast material. Unsuitably buffered acids will increase hydrolysis of plastics. Partial removal of the mold via dissolution of select regions can be achieved using selective spatial application of mold solvents. Table 1 lists suitable solvents for some processing methods.

TABLE 1

| Mold Material | Cast Material | Processing Method | Solvent |
|---|---|---|---|
| Wax | α-hydroxyacids | Solvent | Hexane |
| Polysulphonamide | Silicone | Uncured material | Acetone |
| Ceramic | Polyurethane | Solvent | Acid |
| Ceramic | α-hydroxyacids | Melt | Acid |

For ceramic molds, only solvent dissolution was possible. Molds were placed in RDO (APEX Engineering Products Corp, Plainfield, Ill.) under fluid agitation for 1–6 hours. Complete mold removal was verified by x-ray. For HA/PLA composites, the ceramic was selectively removed using a surface etching technique. The cast structures were embedded in wax and the wax selectively removed from surfaces where ceramic erosion was to occur. The depth and uniformity of erosion was regulated by exposing different regions of the surface over time to RDO and adjusting the time in RDO. The eroding ceramic struts that defined polymer pores were cleaned of ceramic particles with pressurized air several times during etching. The scaffolds were then washed with distilled $H_2O$ and dehydrated in graded ethanol washes.

Fourth, a process for porogen removal may be used. Hydrated solvents can be used to remove salt and sugar porogens. During the process of ceramic leaching, salt porogen particles are removed as well. Hydrated solvents were used to remove salt porogens. For ceramic mold, salt particles were removed by RDO soaking. For wax molds, scaffolds were hydrated using 15 minute washes in the following order: 1:1 (cyclohexane:ETOH), ETOH, 19:1, 17:1, 14:1, and 6:1 (ETOH:$H_2O$), and $H_2O$. Soaking the molds in $H_2O$ for 48 hours removed the salt. Scaffolds were then dehydrated in ethanol washes.

According to another aspect of the method of the present invention, defined chemistry for molecule adhesion on 3D scaffolds can be implemented. That is, scaffolds can be modified with specialized molecular species in order to facilitate substrate dependent chemistry, ligand attachment, cell culture in vitro, and engineered tissue and organ implant fabrication and host integration via control of seeded or migrating cell function.

Three examples of processes for functionalization of scaffolds surfaces are now detailed. Some of the presented methods are only applicable to Sylgard (a silicone) and other plastics that cure using similar addition chemistry.

According to the first technique, functional activation is performed via adsorption. For example, a buffered solution is used to adsorb solubilized ligand onto the scaffold surface. The adsorption is regulated by the hydrophobicity and surface charge of the scaffold material. This technique does not yield a stable surface.

According to the second technique, functional activation is performed via addition reaction. For example, a novel Sylgard functional activation technique may be used. This technique utilizes amide chemistry to bind cell ligands or other chemical species to the silicone surface that has been derivitized with carboxylate and amine moieties. This functional activation can be performed under several conditions, two of which are outlined below.

In the first functional activation condition of the second functionalization technique, the mold used to cast the silicon is coated with a vinylated carboxyl or amine derivitizing compounds (e.g., acrylic acid, vinylacetic acid, 4-pentenoic acid, allylamine, acrylamide). The Sylgard is then poured into the mold. The derivitizing agent becomes covalently bonded to the Sylgard during curing. This occurs because the vinyl groups of the derivitizing compounds react with electrophilic Si groups in Sylgard via addition under a platinum (Pt) catalyst. The desired ligand is covalently coupled to the derivitizing agent. An example amide chemistry employed to achieve covalent coupling utilizes 1-[3-(dimethylamino)propyl]-3-ethylcarbodiimide hydrochloride (EDC). The benefit of this derivitization method is that it utilizes the cross-linking chemistry of Sylgard. Sylgard cures via addition cross-linking between nucleophilic dimethylvinyl-terminated polydimethylsiloxane and electrophilic methylhydrogen siloxane groups. The Sylgard prepolymer contains the Pt catalyst.

In the second functional activation condition of the second technique, the vinylated derivitizing compounds are mixed and allowed to cross-link with the Sylgard curing agent. Since the derivitizing compounds contain only one vinyl group, no cross-linking occurs between curing agent molecules and the mixture remains liquid. The stochiometry of the reaction is regulated such that free methylhydrogen siloxane groups remain available for cross-linking with the Sylgard base material. The curing agent/derivitizing molecule mix is then added to the Sylgard base material and allowed to cure. The desired ligand is covalently coupled to the derivitizing agent. The second method is better suited to create functionally activated surfaces using conventional porogen leaching micro-pore fabrication techniques.

According to the third functionalization technique, surface modification is performed via plasma activation, derivitization, and subsequent functionalization via covalent modification. For example, the silicone surface is first activated via plasma discharge. Plasma discharge is also referred to as glow discharge or radio-frequency (RF) discharge. Plasma activation is applicable to more materials than the Sylgard chemistry outlined above (e.g. poly($\alpha$-hydroxyacids), poly(anhydrides), poly(propalenefumarates), polycaprolactone, polyurethanes, and silicones). Therefore, this technique, as defined by the amide chemistry functional groups used, can be used to functionally activate several materials for cell attachment, including silicone substrates currently used in cell culture (e.g., Flexcell International Corp cell culture plates, Hillsborough, N.C.).

The plasma derivitization is preferably performed under two conditions, direct deposition of the derivitizing group within the plasma chamber or plasma ionization of the surface within the plasma chamber and subsequent addition of the derivitizing group external to the chamber. In the first plasma derivitization technique, the vinylated functional compound or compounds is placed along with the silicone in the plasma chamber. The functional compound is vaporized under plasma. The vinyl groups then react with the ionized silicone surface produced under plasma. The plasma methods and gases to be used can be varied (e.g. microwave or glow discharge using argon or xenon).

In the second plasma derivatization technique, the silicone is subject to plasma such that the surface becomes oxidized. This can be achieved with a small amount of oxygen gas in the plasma chamber or by exposing the silicone to an oxygen atmosphere after plasma modification. The vinylated derivitizing molecule is then covalently bonded to the silicone surface using EDC and/or tosylation chemistry. The functionalized surface may also be stabilized by coupling functionalizing molecules to each other using a similar technique as above.

According to yet another aspect of the present invention, a process for stabilization of modified surfaces yielded using the second and third functionalization techniques is provided. Derivitizing molecules are subject to material surface rearrangements when they are covalently coupled to the material. The derivitized surface is stable under low surface energy interfaces like water and cell culture media. When exposed to air, however, the surface energy increases. The derivitizing groups may then be internalized into the material. This internalization process is driven by the thermodynamically favorable decrease in enthalpy and increase in entropy.

In order to stabilize the derivitized surface, derivitizing groups can be covalently coupled to each other via a primary cross-linker. Consequently, the derivitizing groups cannot be internalized because the cross-linker inhibits bond rotation of the polymer backbone. In order to maintain versatility to attach any desired cell ligand or chemical species using amide chemistry, the primary crosslinker should also contain active carboxyl and/or amine sites. Ideal molecules include, but are not limited to, polylysine, polyarginine, polyapartate, and polyglutamate. These molecules may be linked to the active carboxyl and amine groups of the derivitizing molecule directly using EDC to activate carboxyl groups or indirectly using secondary cross-linkers such as formaldehyde and glutaraldehyde. Cell ligands and other chemical species can be covalently bonded to the primary crosslinkers via the same EDC and secondary cross-linker chemistry.

Control over molecular orientation on the material surface is also desirable. For example, the orientation of cell attachment ligands has been shown to regulate cell binding. Additionally, immobilized enzymes function best if the active site is not occluded by the material surface. Control over orientation of immobilized molecules is possible using the covalent functional activation techniques presented herein. The adsorption method does not afford this control. By altering the use of crosslinkers and EDC, the steric orientation of cell attachment ligands can be inverted. For example, the cell attachment molecule GRGDS (glysine-arginine-glysine-aspartate-serine) can be attached to a surface with the amine or carboxyl end facing away from the surface.

Except for the functionalizing method where the derivitizing molecule is added to the curing agent, the above functionalizing methods only alter surface properties of the desired material. Therefore, the bulk properties a material such as elastic modulus and degradation rate are maintained. This makes these methods more favorable than bulk material modification methods.

Several simulations and working models of the present invention will now be described.

First, a 3D silicone and/or hydroxyapatite (HA) ceramic cell culture substrate with cell adhesion ligands will be described with reference to FIGS. 18–21. 3D micro/macro-porous scaffolds for anchorage dependent cell culture have been manufactured in accordance with the teachings of the present invention. High-density cell cultures can be achieved in small volumes using these scaffolds.

Figure 19:
FIG. 19 shows cell adhesion and spreading on uncoated Sylgard after 1 hr. (Sylgard does not support good cell adhesion without surface modification)
Figure 20:
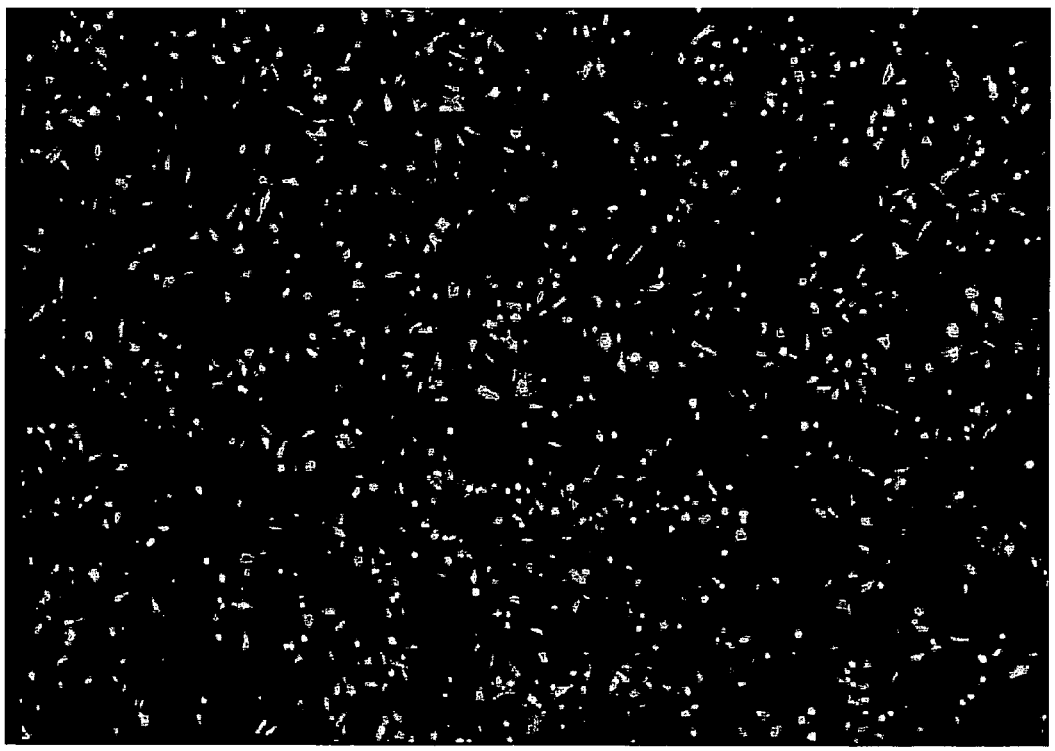
FIG. 20 shows cell adhesion and spreading on fibronectin coated HA after 3 hrs.(cells were allowed to adhere over 1 hr and then the HA surface was inverted, only adherent cells remained and were then allowed to spread for 2 hrs.)
Figure 21:
FIG. 21 shows cell adhesion and spreading on uncoated HA after 3 hrs. (the same procedure was used as FIG. 16, cell spreading is much lower on untreated HA)

The macro-porous network is designed to facilitate nutrient diffusion and waste clearance and provide a network for perfusion assisted mass transport. This in turn enhances cell viability and function. The surfaces of these scaffolds are then derivatized with cell adhesion ligands. Together with the scaffold material, select adhesion ligands can be used to control cell proliferation and biosynthesis rates, including extracellular matrix and soluble protein production. Sylgard and HA scaffolds functionally activated with fibronectin (FIGS. 18 and 20) display enhanced cell adhesion and spreading compared with their respective counterparts without functional groups (FIGS. 19 and 21).

Advantageously, the cell culture scaffolds presented may be reused, depending on the fabrication material selected. However, several cell attachment ligands may be damaged by cell culture passaging methods. In order to maintain predefined surface chemistries, these structures would preferably be recoated. Since most of the surface derivitizing molecules are stable under common digestions used during cell passage (e.g. trypsin, ethylenediaminetetraacetic acid, and collagenase), the materials only need be recoated with attachment ligands.

Second, it is predicted that the present invention will be suitable for fabrication of an immobilized cell/enzyme biosensor.

Third, the present invention may be used to fabricate structural prosthetics: plastic/(ceramic/cement) composites for bone and soft tissue. As an example, a ceramic/polymer composite for tendon and ligament replacement will be described. Composite ceramic/plastic polymer scaffolds have been fabricated for replacement of damaged ligaments and tendons in accordance with the teachings of the present invention. Several designs have been created that consist of three parts: the rigid base, the interface region, and the flexible plastic polymer block.

The materials used to fabricate the scaffold may be HA and $\alpha$-hydroxyacids, all FDA approved materials for human implant use. The scaffold long axis traverses from the base, through the interface region, and along the polymer block.

The ceramic base is designed to be implanted into bone at the tendon insertion site. It contains a macro-porous architecture designed to promote angiogenesis, bone ingrowth, and anchoring of the implant into bone. The ceramic base can be fabricated with a screw shaped external architecture so that initial bone anchoring is provided via surgical screwing into place. The base can also be fabricated with holes for initial bone anchoring with screws or pins. After bone ingrowth and tissue anchoring of the base occurs, the screws or pins may be removed or resorbed.

The polymer block consists of longitudinal polymer fibers that are interconnected through an off axis lattice network. The longitudinal fibers carry the tendon and ligament tensile loads. The interconnecting lattice provides some load transfer between fibers and block structural rigidity in the off axes. The lattice network can be orthogonal to the scaffold long axis. Several lattice networks are suitable. The interspace between fibers is composed of locally porous polymer that serves as a carrier for cells and a template for cell migration and tissue ingrowth. Alternatively, the interspace may be filled with a polymer gel such as collagen type I, fibrin, or alginate.

A preferred lattice consists of individual struts interconnecting longitudinal fibers at an acute angle, akin to trusswork. As longitudinal fibers are stretched during loading, the interconnecting lattice deforms and orients along the scaffold long axis, thereby bearing some longitudinal loading. The lattice network carries an increasing percent of the overall scaffold load as the scaffold load increases. This endows the scaffold with nonlinear stiffening behavior. This is beneficial in that it provides a flexible scaffold that behaves similarly to native tissue and delivers substrate loads to cells adherent to the polymer surface, while becoming very stiff at high loads to minimize the risk of scaffold rupturing. Additional designs for the ligament portion that include wavy fibers to match the nonlinear mechanical behavior of ligaments or other soft tissues can be fabricated using this technique.

The polymer block is anchored to the muscle or bone attachment site using surgical sutures, staples, or screws. However, the ligament scaffold can be fabricated with two ceramic bases at both ends, avoiding the use of staples or screws during surgical implantation. This is possible because ligaments have two bone insertion sites at each end. These ligament scaffold ends are anchored into the two bone insertion sites occupied by the damaged ligament.

The interface region is composed of the polymer fibers anchored in the ceramic base through an interconnected network. A preferred interface design consists of ellipsoidal longitudinal channels interconnected with orthogonal links. The ellipsoidal structure and orthogonal links increase the pullout strength of the fibers from the ceramic base.

Figure 22:
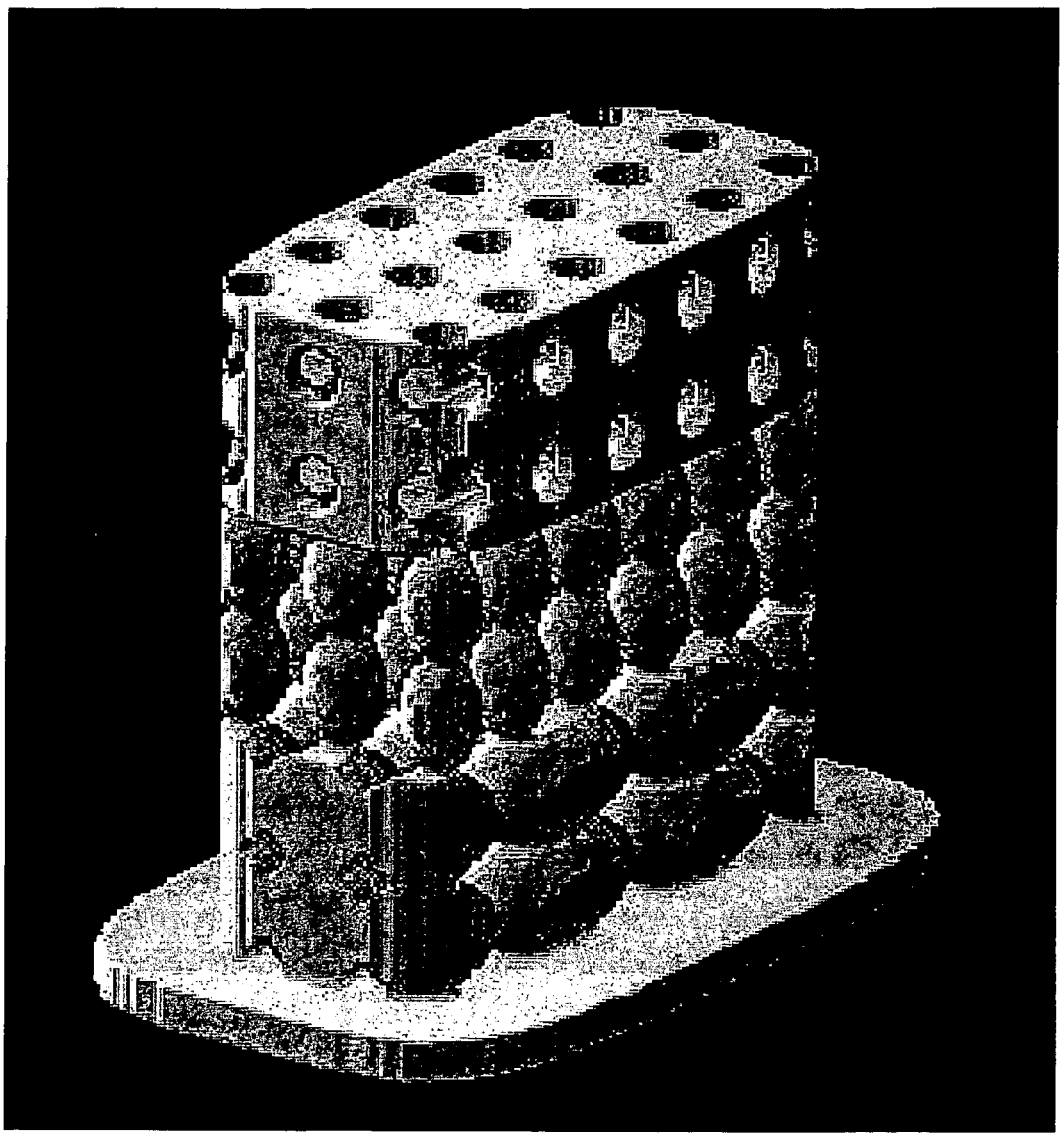
FIG. 22 shows a mold design for HA/PLLA composite scaffold (ellipsoidal pores in the middle band are where PLLA is cast and anchored within the HA scaffold)

The above scaffolds have been manufactured from HA/PLLA and the design of the polymer ceramic interface shown in FIG. 22. In order to match natural ligament or tendon properties while maximizing scaffold flexibility and ultimate strength, a composite HA/(PLGA+PU) scaffold has also been designed. This scaffold design consists of a polymer block containing both PLLA and PU fibers interconnected via exclusive lattice networks. Both the PLGA and PU fibers carry load. However, the PU fibers are more flexible than the PLLA fibers. As new tissue grows into the scaffold after implantation, the PLLA fibers are resorbed. This removes some of the mechanical load carried by the scaffold in vivo and distributes the loading to the ingrown tissue. This is desirable in order to ensure adequate mechanical properties of the regenerate tissue.

Fourth, the present invention can be used to create a ceramic/plastic composite for joint resurfacing. Diarthroidal joint resurfacing and construction of living artificial joints is hampered by the lack of tissue integration with preexisting host tissue, inadequate mechanical properties of the regenerate cartilage, and failure at the bone/cartilage interface. Methods similar to the ligament/tendon engineering methods have been developed in accordance with the teachings of the present invention to fabricate cartilage implants with a ceramic/cement base. This method allows for the entire resurfacing of joints as the implant becomes anchored to the subchondral bone bed via bone ingrowth into the ceramic base.

Again, the implant consists of three parts: the rigid base, the interface region, and the flexible plastic polymer bloc. The ceramic base is similar to the ligament/tendon base and may be manufactured from HA, an FDA approved material. It can be fabricated to encompass an entire joint surface. Referring again to FIGS. 14–17, a porous discrete composites fabricated according to the present invention includes regions of pure sintered ceramic (HA), pure polymer (PLA, PGA), and combinations of the two in the same scaffold are shown. Such discrete composite scaffolds may be useful for structural and interface tissue engineering for several reasons. Both scaffold material and stiffness is regionally controlled within one scaffold. A broad range of materials may be used, including dense sintered HA. With the present methods, the composite materials are interdigitated for increased mechanical integrity, a requisite for bone/cartilage, bone/tendon, and bone/ligament engineering. Together, these advantages coupled with precise control over scaffold external geometry and internal global-pore architecture provide enhanced control over scaffold mechanical properties, biologic effects, and degradation kinetics. As an example of how these scaffolds could be used for bone/cartilage interface engineering, the PLA/HA composite was designed for use in an orthotopic defect model (see FIGS. 14–15). The polymer wall surrounding the periphery of the polymer half serves to entrap seeded chondroblasts and prevent migration of osteoblasts into the polymer region, preventing bone formation where cartilage growth is intended. Conversely, osteoblast migration and bone production is possible in the HA region.

On the other hand, in the case of cartilage engineering, the polymer block is a sponge with defined local/global-porosity that provides mechanical force support and load transfer to the ceramic block. The sponge may be used to carry cells and/or contain hydrogels. In the preferred embodiment, the scaffold is loaded with chondrogenic cells during implantation. Several sources for these cells are well known.

The cells can be delivered without carriers or in secondary gels. The cells produce a cartilagenous matrix in vivo providing full load bearing capability and mechanical function by the implant. The hydrogels, including polyvinyl alchohols, polyethylene glycols, alginates, and pluronics (PEO-PPO-PEO, i.e. PEO=poly(ethylene oxide), PPO=poly(propylene oxide)), can be used to enhance maintenance of chondrogenic cell phenotype and mechanical load bearing. The polymer bloc sponge can be made of α-hydroxyacids that are FDA approved. The preferred polymer bloc material is PLGA, as the increased hydrolytic rate of the polymer enhances chondrogenic phenotype.

The interface region consists of a pore network within the ceramic base into which the polymer sponge interdigitates and is anchored. Pores may be fabricated that allow osteogenic cells from the base and chondrogenic cells from the polymer block to access the same volume and produce a natural cartilage/bone tissue interface, further enhancing the integration of cartilage and bone tissues.

Fifth, the present invention may be used to create a living ceramic/plastic composite for ligament replacement. Autologous ligament/tendon transplant is the gold standard for current ligament/tendon replacement. However, there are two major limitations of this method. First, the donor tissue site suffers from decreased mechanical strength and function while the risk of site morbidity increases. Second, the implanted tissue's mechanical property degrades post-implantation due to cellular degradation of the implant matrix secondary to decreased functional loading. The loading of the implant must be limited post operatively in order to assure implant integration into the host tissue. However, if the ligament/tendon transplant can be engineered to provide immediate mechanical functionality and integration with host tissue, the risk of implant degradation is minimized.

The ligament/tendon scaffolds presented above provide immediate mechanical integration with the host tissue. Additionally, these scaffolds can be pre-seeded with cells in vitro and pre-conditioned to produce tissue with similar mechanical properties to natural ligaments and tendons, thereby providing immediate natural functionality. These scaffolds can be created from HA/PLGA, currently FDA approved implant materials. The PLGA lactide/glycolide ratio used is chosen such that the polymer has been degraded prior to implantation. Three methods to create living ligament/tendon constructs are presented as examples.

In the first construction method for the living ceramic/plastic composite ligament replacement, the polymer block is seeded with fibroblasts. These cells can be derived from the patient or from universal cell lines. The cell are seeded within a carrier matrix that fills the space between polymer fibers. Several carriers can be used, including but not limited to collagen gels, fibrin clots and alginate. A preferred design utilizes a collagen type I carrier. The scaffold is then placed in a bioreactor and subject to tensile mechanical load conditioning and perfusion of culture media. The mechanical loading influences the extracellular matrix production of the cells and yields a stiffer tendon structure than otherwise possible in culture. The perfusion is initially used to maintain cell viability.

As the amount of extracellular matrix increases in the scaffold, the number of cells decreases. The decreased metabolic demand of the tissue coupled with then forced perfusion induced by mechanical loading of the scaffold eliminates the need for perfusion of culture media over time.

In the second construction method, the polymer scaffold is seeded with a gel carrier containing stromal cells derived from the patient bone marrow or from a universal stromal cell line. These cells have been shown to produce connective tissue in vitro. The cells are induced to produce fibrous tissue using two methods. First, the culture media may be supplemented with basic fibroblast growth factor and/or connective tissue derived growth factor (CTGF) that induces increased stromal cell collagen I secretion and fibrous matrix production. Second, the cells are infected to produce CTGF and thereby signal increased fibrous tissue production via paracrine/autocrine pathways. The cells are infected with an adenovirus created with Cre-lox recombination according to a known method carrying an expression vector for CTGF coupled to a cytomegalovirus (CMV) promoter (AdCM-VCTGF). The transfection is transient, minimizing the risk of immunological rejection post implantation in the host.

The cells may be transfected under three different protocols. First, the cells can be transfected in vitro before seeding onto the scaffold. Second, the scaffold may be coated with virus and the cells seeded onto the scaffold. The virus may be covalently liked to the scaffold surfaces using the chemistries outlined above. Third, the virus and cells can be mixed into the gel carrier and then seeded onto the scaffold. In the latter methods, cell infection occurs either in vitro or in vivo after scaffold implantation. The scaffold is then placed in the bioreactor and subject to tensile mechanical load conditioning and perfusion of culture media.

The third construction method is similar to the second, except that non-stromal cells are used. These cells are induced to produce connective tissue using the AdCM-VCTGF virus as outlined above. The adenovirus is replication deficient and the expression of CTGF is transient. Therefore at implantation time, the implant tissue does not produce any exogenous drug and therefore may not considered a pharmaceutical but rather a biological. The implant may also be devitalized with freeze/thaw processing rendering it a medical device. Devitalizing the construct would render a structure similar to allogenic tendon/ligament transplants albeit with enhanced mechanical integration into the host site.

The scaffold is ready for implantation after mechanical load conditioning during in vitro culture. The bioreactor can monitor tissue stiffness increase over culture time and this information may be used to discern when adequate tissue stiffness has been achieved. Prior to implantation, the ceramic base of the scaffold may be seeded with bone-derived osteoblasts and/or bone marrow stromal cells to enhance the rate of bone formation and tissue anchoring of the implant. These cells may be seeded with or without gel carriers.

Sixth, the present invention may be used to provide a living ceramic/plastic composite for joint resurfacing. The scaffold fabricated for joint resurfacing may be pre-seeded and mechanically conditioned in vitro in order to produce tissue with similar mechanical properties to natural joint cartilage, thereby providing immediate natural functionality. Cells may be seeded directly onto the polymer sponge or in secondary gel carriers. The preferred gel for cell seeding is collagen type I & II/chondroitin gel that resembles the natural cartilage tissue constituents. The gel is manufactured by solubilizing collagen types I and II in acetic acid, adding chondroitin sulfate, diluting the mix to an appropriate concentration in cell culture media supplemented with sodium bicarbonate, neutralizing with a biocompatible base, suspending cells, and allowing gellation to occur. The chondroitin sulfate concentrations are low enough to prevent complete precipitation of the collagen from solution.

Alternative gels include but are not limited to collagen I (±II)/hyluronan, fibrin/hyluronan, and fibrin/chondroitin. Collagen II sponges have been shown to induce chondrogenesis by bone marrow stromal cells when compared to collagen I sponges. Multiple cell sources may be used, including differentiated chondrocytes, stromal cells driven to a chondrogenic phenotype via chondrogenic media supplements and culture conditions (including insulin, transforming growth factor beta, basic fibroblast growth factor, dexamethosone, dextran sulfate, micromass culture, and spherical cell culture), and cells transfected to progress along the chondrogenic phenotype, including stromal cells and fibroblasts. The cells may be derived from the patient or from universal cell lines. After seeding, the scaffold is placed in the bioreactor and subject to compressive mechanical load conditioning and perfusion of culture media. The mechanical loading influences the extracellular matrix production of the cells and yields a stiffer cartilage tissue with higher glycosaminoglycan content than otherwise possible in culture. As the amount of extracellular matrix increases in the scaffold, the number of cells decreases.

The decreased metabolic demand of the tissue coupled with then forced perfusion induced by mechanical loading of the scaffold eliminates the need for perfusion of culture media over time. The bioreactor can monitor tissue stiffness increase over culture time and this information used to discern when adequate tissue stiffness has been achieved. Prior to implantation, the ceramic base of the scaffold may be seeded with bone-derived osteoblasts and/or bone marrow stromal cells to enhance the rate of bone formation and tissue anchoring of the implant. These cells may be seeded with or without gel carriers.

Seventh, the present invention may be used to provide scaffolds with designed branching channels for guided blood vessel ingrowth. In this technique, seeding of angiogenic cells is unnecessary. The scaffold global-pores are designed to facilitate nutrient diffusion and blood vessel ingrowth by providing a less tortuous path for cell migration. The local-pores are spaced so that ingrown blood vessels penetrate the entire scaffold. Angiogenic cells may be preseeded into the global pores to facilitate blood vessel formation.

A paramount requirement for survival of implanted living tissue constructs is adequate nutrient supply to the cells. Most tissue-engineered constructs rely on diffusion for transport of nutrients and waste. However, diffusion is unsuitable to large tissue construct fabrication. Molecule diffusion rates depend on diffusing media and the molecular species. Dense tissue have lower diffusion rates compared with less dense tissues. Additionally, the cells have different nutrient demands, depending on the cell type and metabolic state. The combination of diffusion rate limitations and cell metabolic demand forces living tissue constructs that rely on diffusion to be small in size. For example, liver cells are highly metabolic. In order for the cells to remain viable, diffusion rates limit thickness of constructs to less than 1 mm. Bone cell constructs have similar limitations, in particular due to the density of the tissue. Contrarily, cartilage tissue can be made much thicker, for example 1 cm, because the chondrocytes have a much lower metabolism. In order to circumvent this limitation, the tissue construct has to be designed and fabricated with pores for force perfusion or with blood vessels that will carry nutrients and waste.

Eighth, similar scaffold design and fabrication principles as used in the seventh embodiment can be used to fabricate living branching blood vessel template onto which any cells can be seeded. Such a device will facilitate in vitro production of living organ systems. Additionally, such a device will facilitate survival of the living construct once implanted in the host.

The manufacturing methods outlined in this application allow for the fabrication of scaffolds with global-pores that may be seeded with angiogenic cells. Endothelial cells can be seeded in these macro-pores in order to form blood vessels via angiogenesis. Pericytes and smooth muscle cells can be used to line the vessels at later time. Conversely, angioblasts can be seeded in these pores to form blood vessels via vasculogenesis. Angioblasts will form a vascular plexus. Upon implantation, the vessel network can be anastomosed with pre-existing vasculature. In order to enhance vessel production, angiogenic biofactors can be incorporated in the macro-pores or bulk scaffold material. VEGF-1 (vascular endothelial cell growth factor) can be used as an angiogenic factor specific to endothelial cells. Additional factors include ANG-1, PDGF-β, and TGFβ. The later have additional effects on cells other than endothelial cells and angioblasts. After blood vessel formation in the scaffold in vitro, the scaffolds are then seeded with cells that will produce the desired tissue type. Nutrient and waste clearance functions are carried out by media perfusion through the engineered blood vessel network that permeates the scaffold with the use of a bioreactor.

The presented methods provide several benefits for the production of living branching blood vessel devices. First, the blood vessel network can be made such that all arterioles branch from one synthetic artery. The same is true for the venial path. This is possible due to the control of pore branching structure afforded by SFF methods. Consequently, the scaffold contains one artery and vein that are anastomosed with a pre-existing artery and vein in the implant site and thereby supply nutrient and waste transport to the entire scaffold. Second, the macroscopic blood vessel structure can be fabricated to mimic natural blood vessel constructs using the presented global pore design and manufacturing methods. Third, living tissue constructs can be fabricated in vitro on scaffolds where the scaffold material makes up less than 10% of the scaffold volume. This is possible because the disclosed casting manufacturing technique allows for the fabrication of local-pores. Unlike blood vessel construct fabricated using two dimensional templates, these constructs can be seeded with large amounts of cells in the remaining local-pores. Therefore, the living tissue is not restricted to the global-pores, but the entire scaffold volume. Fourth, the use of angioblasts simplifies the vessel maintenance in vitro because the vascular plexus that is formed can be maintained under static culture media conditions. During in vivo vasculogenesis, the forming vascular plexus is not connected to the systemic circulatory system, unlike the blood vessels formed during angiogenesis.

Ninth, the present invention may be used to provide scaffolds mimicking existing tissue structure. Any tissue structure that can be 3D imaged, including blood vessels via computed tomography (CT) angiography, trabecular bone via micro-CT, and ligaments and tendons via magnetic resonance imaging (MRI) can be replicated from ceramic, cement, and plastic and polymeric materials. Structures created from these image sets can be used to mimic natural tissue function, create tissue replacements, and investigate the contribution of tissue structure on tissue function and adherent cell behavior. In addition, inverse molds of actual tissue structure can be made and tissue grown into the pores of the mold to generate multiple repetitions of actual tissue. For example, a scaffold has been manufactured in accordance with the teachings of the present invention from PLA that replicate trabecular bone architecture. See FIG. 23.

Tenth, the present invention may be used for branching polyurethane vascular stents. These stents are designed to replace branching vessel structures. The present invention may be used to produce a pre-made living branching blood vessel template onto which any cells can be seeded. The present invention may also be used to provide pre-vascularized implantable tissue constructs.

Eleventh, the present invention may provide living tissue constructs for proteomic data, pathogen, and drug screening. For example, one could use living cartilage tissue created with osteoarthritic tissue for screening of therapies. Using the method of embodiment ten, inverse molds of actual trabecular bone structure can be made and tissue grown into the pores of the mold to generate multiple repetitions of actual trabecular tissue for in vitro drug testing. This approach could be used to test osteoporosis drugs on in vitro generated bone tissue.

Twelfth, the present invention may also be used to provide living tissues for drug production and drug discovery using the methods outlined in embodiment eight. That is, living tissue structures can be fabricated that produce therapeutic biofactors. In this application, cells that produce the desired biofactor are seeded onto the vascularized scaffold in vitro. For biofactor production, the scaffold is maintained in vitro and the biofactor harvested. A vascularized scaffold is not required for biofactor production in vitro. In this case, the global channels will serve for nutrient perfusion and drug harvest. For therapeutic delivery in vivo, the tissue construct is implanted and anastomosed with preexisting vasculature. An example of this is the delivery of Factor IX to treat hemophilia B.

Hemophilia is a sex-linked hereditary bleeding disorder transmitted on a gene of the X chromosome. Persons with hemophilia have prolonged bleeding when injured due to reduced functional amounts of one or more of the plasma proteins needed to form a clot. Hemophilia B, which is sometimes called Christmas disease, is a condition in which the body does not make functional Factor IX. Factor IX is an antihemorrhagic protein that participates in the blood clot cascade. Factor IX isolated from donor plasma and recombinant Factor IX are used to treat Hemophilia B, and in some cases Hemophilia A, via systemic injections. These treatments are designed to stop blood loss after it has begun. However, a more desirable treatment should inhibit the spontaneous bleeding that often occurs in hemophilia. This can be achieved by maintaining normal levels of Factor IX in the system circulation. Delivery via implantable pumps or doped materials is impractical because Factor IX has a short storage life once reconstituted. Therefore, delivery of Factor IX via an implantable tissue construct is ideal. In this therapy, bone marrow stromal cells are isolated from the patient and expanded in culture. The cells are transduced to produce Factor IX. These cells are then seeded on a pre-vascularized tissue template to create a mass of tissue that produces Factor IX. This tissue consists of fibrous tissue and bone surrounding the predefined vessel structure. The living tissue construct is implanted into the patient and anastomosed, whereupon systemic delivery of Factor IX commences. The implant is immunocompatible as the patient's endogenous cells are used. Additionally, the stromal cell transfection occurs ex vivo. The architecture of the tissue construct, both external shape and internal pore structure, regulates the tissue mass and vascular access, thereby regulating the amount and rate of Factor IX released. Depending on the patient size, the scaffold template is adjusted accordingly. The construct is radiographically identifiable since it contains bone tissue. Therefore, the construct can be surgically retrieved should necessity arise.

The disclosed indirect SFF scaffold manufacturing methods provide versatility because assorted scaffold designs, materials, and casting methods can be used. Such versatility is not possible with direct SFF techniques. This is essential for tailoring designs to meet specific tissue engineering applications. Compatible materials include ceramics, cements and polymers such as silica, hydroxyapatite, plastics and polymers (e.g. α-hydroxyacids, polycaprolactone, polyanhydrides, polymethylmethacrylate, polypropylenefumarate), rubbers (e.g. polyurethane, polydimethylsiloxane), biological materials (e.g. collagen, alginate, fibrin and dextran gels), and composites thereof. Compatible polymer processing techniques include melt processing, emulsion freeze drying, emulsion solvent diffusion, phase separation and freeze drying, solvent casting and particulate leaching, gas foaming, and combined gas foaming and particulate leaching. Each processing method has advantages that suit different tissue engineering applications.

The outlined methods of the invention contain several other inherently useful properties that contribute to the utility of the presented embodiments above.

For example, melt processing yields dense and tough polymer structures ideal for load bearing tissues but precludes the incorporation of biofactors within the polymer phase as is possible with gas foaming. In these methods, leaching of porogens was facilitated by the presence of the interconnected global pores, allowing the removal of salt from relatively thick scaffolds. Porogen leaching from thick scaffolds is often difficult because solvent permeability is low when the porogen is present. Additionally, 3D molds containing global pore templates provide for casting of larger local pore scaffolds than possible when casting in hollow containers.

Most local-pore fabrication technology is not compatible with direct SFF fabrication methods. For instance, the use of emulsion, phase separation, solvent diffusion, and gas foaming local-pore fabrication techniques is not possible with direct 3DP, SLS, STL, DMD, LOM, and FDM. In contrast, porogen leaching can be used with these methods. For example, 75% and 90% void fraction PLA scaffolds have been made with controlled local pore size ranging from <38–150 μm using TheriForm™ (a 3DP system, Therics, Princeton, N.J.) and salt leaching. However, high local porosity, which is a function of void fraction and pore interconnectivity, is difficult to achieve in direct SFF. In particular, the distance between porogens increases during extrusion in FDM. In STL and SLS, the light beam used may diffract through large porogens, adversely affecting curing and melting. Finally, the densely packed porogen bed necessary in 3DP for high porosity may interfere with powdered build material salvation and binding. As noted, high pore interconnectivity is required to promote cell and tissue growth. In 3DP manufacturing, local pore interconnectivity may be improved by using volatile porogens that sublimate upon contact with solvents or direct polymer deposition upon an interconnected porogen bed. Such methods are also compatible with indirect 3D scaffold fabrication via casting. Nevertheless, it is the ability to employ varied polymer and porogen processing techniques using indirect SFF fabrication that facilitates construction of high porosity scaffolds.

Solvent casting and injection molding of blend composites are also feasible with indirect SFF casting methods. Blend composites offer greater resistance to fatigue, increased ceramic resorption rates, and facilitated biofactor adhesion compared to conventional 100% ceramic scaffolds. Direct SFF methods may also be used to manufacture blends. For example, local pore 80:20 PLGA:TCP scaffolds have been made using TheriForm™ and salt leaching. Additionally, using SLS and 3DP, graded composites with gradients in ceramic concentration may be manufactured by altering the polymer to ceramic ratio between bed material layers. However, composite manufacturing with 3DP, STL, and FDM is limited because these methods require incorporation of binders within the entire scaffold ceramic region, use a low ceramic volume ratio, or have inadequate bonding of the polymer and ceramic regions. These direct SFF methods preclude the use of sintered ceramic and the fabrication of discrete polymer/ceramic scaffolds.

The use of sintered dense ceramic is desirable for several reasons. The polymers in blends may interfere with the osteoconductivity of HA. In fact, calcium phosphates have been nucleated onto polymers in the hope of increasing osteoconductivity. Unlike polymers, HA exhibits direct collagen and bone apposition with a strong mechanical interface between ceramic and bone. This concept has been used to improve bone/polymer bonding strength via incorporation of HA in PLA. Finally, although sintered HA is much stiffer than cortical bone, porous HA scaffolds with similar porosity and compressive modulus of trabecular bone have been made. Blends have commonly been manufactured as bone fillers or as non-porous bone fixation devices with stiffness similar to cortical bone and bending strengths of similar order of magnitude. However, the diminished load bearing capability of porous blends may make them more suitable for non-load bearing applications.

50–65% porous ceramic scaffolds made from replamine form coralline have successfully been used for hard tissue repair (ProOsteon and Interpore, Interpore Cross International, Inc. Irvine, Calif., for review). Coralline compressive modulus is on the order of trabecular bone modulus, making these scaffolds ideal for hard tissue repair. However, ceramic scaffolds are exceedingly stiff for soft tissue repair, precluding their use for interface tissue engineering. Discrete composites containing dense ceramic for bone growth and polymer for soft tissue growth have been created by adhering PLA fleece to a Coralline™ or calcite substrates. However, their function under physiologic skeletal loads might be inadequate as no mechanical interdigitation or strong chemical adhesion of the composite phases was provided. As shown in FIGS. 14–15, indirect casting provides for fabrication of mechanically interdigitated discrete phase composites and blends thereof. The composites presented herein circumvent the limitations in blend manufacturing, including variable mechanical properties at high ceramic loading, while conferring the desirable biologic and mechanical properties of different materials within the same scaffold.

The utility of biomimetic approaches for scaffold design and fabrication is under investigation. IBD has been used to design temporomandibular condylar prosthesis that replicates the natural condylar shape. Nano-fibrous α-hydroxyacid matrices have been created to mimic natural matrix collagen size and structure. Bio-inspired mineral deposition of carbonated apatite onto α-hydroxyacids has been used to render them osteoconductive. Several groups have developed tubular tissue engineered constructs for blood vessel replacement. These studies have replicated macroscopic (vessels and condyles) and nanoscopic (fibers and crystals) features of naturally occurring tissues. The disclosed methods provide for bio-mimicry on the microscopic and macroscopic scale.

Figure 23:
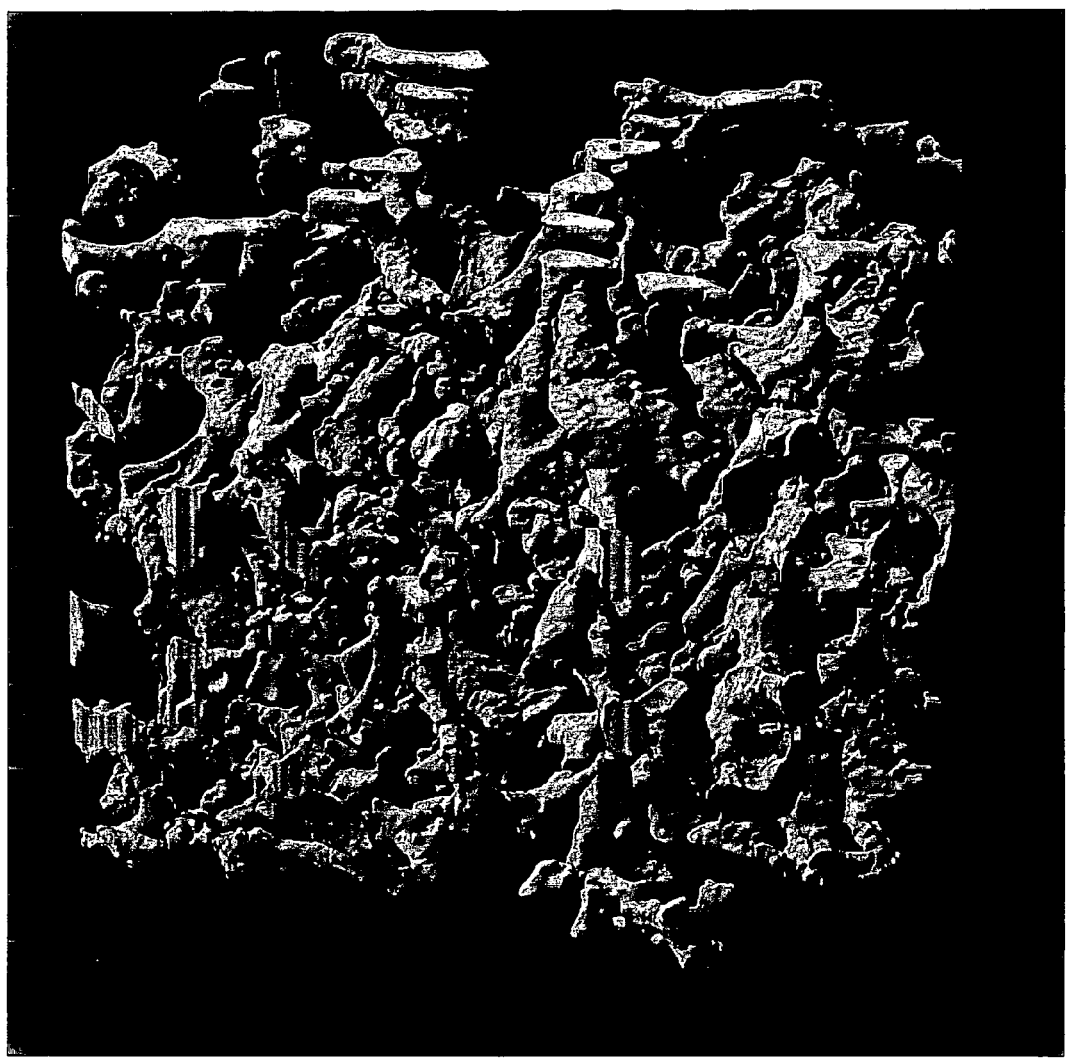
FIG. 23 shows a μCT rendering of a biomimetic PLA scaffold replicating human distal femoral trabecular bone structure (the scaffold was built at 2× scale for imaging requirements)

Referring now to FIG. 23, using the indirect SFF method of the present invention, the microscopic structure of human trabecular bone was replicated. This scaffold was built at twice physiologic size to facilitate visualization on μCT systems. With this technique, scaffolds may be fabricated with complex branching tubular networks that replicate tissue structure and function, like branching blood vessels, kidney tubules, and lung bronchiole.

In view of the foregoing, it can be appreciated that the synthesis of indirect SFF technologies, current scaffold fabrication methods, and image based design provides the means to precisely control scaffold material composition and architecture, including local and global porosity. This control allows for the manufacture of scaffolds for tissue engineering that are optimized for mechanical and biological function through precise manipulation of scaffold shape, porosity, and internal pore architecture (pore size, geometry, orientation, branching, and interconnectivity). This control facilitates engineering of biomimetic scaffolds and scaffolds for complex biomechanical applications, including perfused tissues (concurrent local/global porous scaffolds) and interfaces between bone and soft tissues (ceramic/polymer discrete composite scaffolds). Future scaffolds constructed with these integrated manufacturing techniques should aid tissue reconstruction, regeneration of damaged tissues and organs, artificial organ production and living tissue construct fabrication.

In conclusion, the present invention provides novel casting methods to manufacture three dimensional (3D) structures from diverse materials with designed and controlled local-porous and global-porous internal architectures using solid free from fabrication (SFF) techniques. These methods allow fabrication of mechanically robust porous composite structures containing a number of plastics, polymers, ceramics, cements, and metals, . These structures can be used as tissue regeneration scaffolds, bioreactor culture substrates, perfusion assisted mass diffusion exchangers, biosensors, "lab-on-chips", and living tissue constructs for proteomic, drug interaction, and pathogen analyses. The ability to manufacture scaffolds from diverse materials is essential for tailoring designs for specific applications. The methods presented allow fabrication of scaffolds from more materials than currently possible, including ceramics, cements and polymers like silica, hydroxyapatite, plastics, rubber, biological materials, and composites thereof. Composite structures consist of two formulations: blend structures made from materials embedded within a second material(s) that is used as a binder or structures with discrete regions of differing material composition that are mechanically interdigitated and/or chemically bonded. These manufacturing methods also provide simultaneous control over structure local and global pore architecture, including scaffold pore and strut geometry, orientation, branching, and interconnectivity. Consequently, these manufacturing methods enable the advancement of tissue engineering, biochip, and bioreactor technologies. In particular, the flexibility of manufacturing scaffolds from varied materials with designed macro/micro-porosity provides enhanced control over:

1. Mass transport and heat transfer
2. Cell seeding and distribution
3. Nutrient transport and waste clearance for living cells
4. Regulation of cell functions
5. Surface area for substrate dependent chemistry, cell adhesion, and matrix deposition
6. Scaffold mechanical properties
7. Scaffold permeability
8. Scaffold electrical conductivity
9. Organization and mechanical properties of tissues grown in scaffolds
10. Delivery of mechanical forces to cells
12. Drug production by anchorage dependent cells And allow the fabrication of:
1. Biomimetic scaffolds
2. Highly porous 3D scaffolds for bioreactors, filters, and cell growth/extracellular matrix production with defined channels for blood vessel ingrowth and/or active perfusion
3. Composite 3D structures with strong mechanical interfaces between material phases.
4. Truly three dimensional biosensors (with & without cells), gene arrays, and "lab on chips"
55. Living tissue constructs for drug screening, pathogen analysis, and screening of proteomic data derived compounds The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method of indirectly fabricating a desired structure comprising:
   computationally designing the desired structure;
   fabricating a three dimensional mold for indirectly producing the desired structure;
   casting a material in the mold to form the desired structure;
   removing the mold from the desired structure; and
   imparting a desired surface property to the desired structure in vitro, where said surface property comprises at least one of chemically active and biologically active.

2. The method of claim 1 wherein said step of computationally designing the desired structure further comprises at least one of computer aided design techniques or image based design techniques.

3. The method of claim 2 wherein said imaged based design technique further maps the computationally designed desired structure to a 3D image scan.

4. The method of claim 3 wherein the mold is fabricated directly using said image based design.

5. The method of claim 1 wherein said step of fabricating a mold for indirectly producing the desired structure further comprises at least one of 3D printing, fused deposition, selective laser sintering, stereolithography, layered object manufacturing, and direct material deposition.

6. The method of claim 1 wherein the mold is formed of at least one of wax, plastic, polymer, sugar, ceramic, cement, and metal.

7. The method of claim 1 further comprising producing smaller feature sizes in the structure by at least one of shrinking said mold prior to said casting step and shrinking said desired structure after said casting step.

8. The method of claim 1 wherein said step of casting a material in the mold further comprises at least one of:
   solvent casting in wax;
   solvent casting in plastic;
   solvent casting in polymer
   solvent casting in ceramic;
   solvent casting in cement;
   solvent casting in metal;
   uncured material casting in wax;
   uncured material casting in plastic;
   uncured material casting in polymer;
   uncured material casting in ceramic;
   uncured material casting in cement;
   uncured material casting in metal;
   melt casting in plastic
   melt casting in polymer
   melt casting in ceramics;
   melt casting in cements;
   melt casting in metals
   injection molding in ceramics;
   injection molding in cements; and
   composite material casting.

9. The method of claim 1 wherein said step of removing the mold from the desired structure further comprises at least one of fracturing, melting, and dissolving.

10. The method of claim 9 wherein said step of dissolving further comprises dissolving at least one of a ceramic and a cement mold using a buffered acid solution.

11. The method of claim 1 wherein said desired surface property further comprises at least one of activation, derivitization, and functionalization of the desired structure surface.

12. The method of claim 1 wherein said step of computationally designing the desired structure further comprises designing a global porous architecture for the desired structure.

13. The method of claim 12 wherein said global porous architecture is selected to promote at least one of tissue ingrowth, media perfusion and angiogenesis.

14. The method of claim 12 wherein said local porous architecture is selected to promote at least one of tissue growth, cell seeding, cell delivery, and biofactor delivery.

15. The method of claim 12 wherein said global porous architecture includes branching global channels.

16. The method of claim 15 wherein said channels are interconnected in three dimensional space.

17. The method of claim 15 wherein said channels interpenetrate an interior of said desired structure but remain exclusive of said local porous architecture.

18. A method of indirectly fabricating a desired structure comprising:
    computationally designing the desired structure;
    fabricating a three dimensional mold for indirectly producing the desired structure;
    casting a material in the mold to form the desired structure
    removing the mold from the desired structure, and
    imparting a desired surface property to the desired structure in vitro, where said surface property comprises at least one of chemically active and biologically active;
    wherein said step of casting the material in the mold further comprises production of a local porous structure via the casting step and a global porous structure via the mold shape to impart the desired structure with two levels of internal architecture scale.

19. The method of claim 18 wherein said step of casting the material in the mold further comprises forming a local porous architecture in the desired structure.

20. The method of claim 18 where said casting step further comprises casting a local porous structure within the mold that defines global pores for the cast structure.

21. The method of claim 18 further comprising casting using at lest one local pore fabrication technique selected from:
    porogen leaching;
    emulsion freeze dry;
    phase separation;
    emulsion solvent diffusion;
    supercritical fluid; and
    gas foaming.

22. A method of indirectly fabricating a desired structure comprising:
    computationally designing the desired structure;
    fabricating a three dimensional mold for indirectly producing the desired structure;
    casting a material in the mold to form the desired structure; and
    removing the mold from the desired structure,
    wherein said casting step further comprises a primary casting step wherein a first material is cast into the mold to yield a global porous structure and a secondary casting step wherein a second material is cast within global pores of the global porous structure to create a local porous structure within the global porous structure.

23. A method of indirectly fabricating a desired structure comprising:
    computationally designing the desired structure;
    fabricating a three dimensional mold for indirectly producing the desired structure;
    casting a material in the mold to form the desired structure;
    removing the mold from the desired structure; and
    functionalizing a surface of the desired structure with a desired ligand.

24. The method of claim 23 further comprising coating the mold with a material to impart a pre-selected characteristic to the desired structure.

25. The method of claim 24 further comprising coating the mold with a derivitizing agent prior to casting the desired structure.

26. The method of claim 23 further comprising incorporating a derivitizing agent into an uncured material and then casting the uncured material in said casting step.

27. The method of claim 23 further comprising activation and derivitization of the desired structure by way of plasma activation.

28. The method of claim 23 further comprising covalently linking a desired ligand to the derivitizing agent.

29. The method of claim 28 wherein a stable functionalization is achieved by using a ligand with multiple functional groups that links to multiple derivitizing agents on the structure.

30. The method of claim 23 wherein a stable functionalization is achieved by stabilizing the ligand after said step of functionalizing the desired structure by covalently coupling functional groups of said ligand using a primary crosslinker.

31. The method of claim 23 further comprising orienting the desired ligand.

32. A method of indirectly fabricating a desired structure comprising:
    computationally designing the desired structure;
    fabricating a three dimensional mold for indirectly producing the desired structure;
    casting a material in the mold to form the desired structure; and
    removing the mold from the desired structure;
    wherein said step of casting the material in the mold further comprises production of a local porous structure via the casting step and a global porous structure via the mold shape to impart the desired structure with two levels of internal architecture scale, and wherein said step of computationally designing the desired structure and mold for casting said structure further comprises designing a biomimetic scaffold using imaged based design techniques.

33. A method of indirectly fabricating a desired structure comprising:
    computationally designing the desired structure;
    fabricating a three dimensional mold for indirectly producing the desired structure;
    casting a material in the mold to form the desired structure;
    removing the mold from the desired structure; and
    seeding cells that produce a desired biofactor onto the desired structure.

34. A method of indirectly fabricating a desired structure comprising:

computationally designing the desired structure;

fabricating a three dimensional mold for indirectly producing the desired structure;

casting a material in the mold to form the desired structure; and removing the mold from the desired structure, wherein said material comprises a low-viscosity ceramic slurry including tricalcium phosphate powder, acrylates, dispersants, and initiators.

35. The method of claim 34 wherein:

a particle size of the powder is less than 100 microns;

a viscosity of the acrylates is less than 100 mPa·S; and the dispersants are at least one of anionic and cationic.

36. The method of claim 34 wherein said material further comprises:

40 volume percent tricalcium phosphate powder, a particle size of the powder being about 1 micron in diameter;

a balancing reactive medium in a 50:50 mixture of isobornyl acrylate and propoxylated neopentylglycol diacylate;

a 2.5% cationic dispersant and 2.5% antionic dispersant; and a thermal initiator.

37. The method of claim 34 further comprising an accelerator to allow a curing reaction at room temperature.

38. The method of claim 37 wherein said accelerator further comprises N,N-dimethyl p-toludine.

39. A method of designing a desired structure comprising:

computationally designing the desired structure to support a tissue interface that includes interfaces between soft tissues and interfaces between bone and soft tissue;

fabricating a three dimensional mold of the desired structure;

casting a material in the mold to form the desired structure, said casting step including:

casting first material base with a macro-porous architecture and external geometry selected to promote angiogenesis, bone ingrowth, and anchoring of the structure into bone;

casting a second material interface region on the base, the interface region being anchored in the base through an interconnected network; and casting a third material block on the interface region, the block including longitudinal fibers interconnected in an off axis lattice network;

removing the mold from the desired structure.

40. The method of claim 39 wherein the interface region further comprises ellipsoidal channels interconnected with orthogonal links.

41. The method of claim 39 wherein the block includes locally porous material between the longitudinal fibers.

42. The method of claim 39 wherein the interconnecting lattice network further comprises a non-linear strain providing structure.

43. The method of claim 39 wherein a lattice network is formed orthogonal to a long axis of the desired structure.

44. The method of claim 39 wherein the lattice network includes individual struts interconnecting the fibers at acute angles.

* * * * *